US005961977A

United States Patent [19]

Hafler et al.

[11] Patent Number: 5,961,977
[45] Date of Patent: Oct. 5, 1999

[54] METHOD OF TREATING OR PREVENTING AUTOIMMUNE UVEORETINITIS IN MAMMALS

[75] Inventors: David Allen Hafler, Newton, Mass.; Robert B. Nussenblatt, Bethesda; Alan G. Palestine, Potomac, both of Md.; Howard L. Weiner, Brookline, Mass.

[73] Assignees: AutoImmune Inc., Lexington, Mass.; The United States of America as represented by the Department of Health and Human Services, Washington, D.C.

[21] Appl. No.: 08/419,505

[22] Filed: Apr. 10, 1995

Related U.S. Application Data

[63] Continuation of application No. 08/324,368, Oct. 17, 1994, abandoned, which is a continuation of application No. 08/178,461, Jan. 6, 1994, abandoned, which is a continuation of application No. 08/052,826, Apr. 23, 1993, abandoned, which is a continuation of application No. 07/928,881, Aug. 4, 1992, abandoned, which is a continuation of application No. 07/809,206, Dec. 13, 1991, abandoned, which is a continuation of application No. 07/551,632, Jul. 10, 1990, abandoned, which is a continuation-in-part of application No. 07/379,778, Jul. 14, 1989, abandoned.

[51] Int. Cl.⁶ .......................... A61K 39/00; A61K 39/38; A61K 38/00; C07K 5/00
[52] U.S. Cl. ..................... 424/184.1; 514/12; 530/304; 530/325; 424/185.1
[58] Field of Search .......................... 424/184.1; 514/12; 530/324, 325

[56] References Cited

FOREIGN PATENT DOCUMENTS

| WO88/10120 | 12/1988 | WIPO | A61K 39/00 |
| WO91/01333 | 2/1991 | WIPO | C07K 13/00 |
| WO91/08760 | 6/1991 | WIPO | A61K 37/12 |

OTHER PUBLICATIONS

Faure, Jean–Pierre et al., Cellular and humoral reactions to retinal antigen; specific suppression of experimental uveoretinitis, Proceeding 'Immunology of the eye; Workshop: II', Eds. Helmsen, R.J., Suran, A., Gery, I. and Nussenblatt, R.B., Sp. Supp. Immunology Abstracts, 1981, pp. 33–48, 1981.
Ben–Nun, A. et al., "The Rapid Isolation of Clonable Antigen–Specific T Lymphocyte Lines Capable of Mediating Autoimmune Encephalomyelitis," Eur. J. Immunol 11:195–199 (1981).
Bitar, D.M. and C.C. Whitacre, "Suppression of Experimental Autoimmune Encephalomyelitis by the Oral Administration of Myelin Basic Protein," Cell Immunol. 112:364–370 (1988).
Caspi, R.R. et al., "T Cell Lines Mediating Experimental Autoimmune Uveoretinitis (EAU) in the Rat," J. Immunol. 136:928–933 (1986).
De Kozak, Y. et al., "Prevention of Experimental Autoimmune Uveoretinitis by Active Immunization with Autoantigen–specific Monoclonal Antibodies," Eur. J. Immunol. 17:541–547 (1987).
De Kozak, Y. et al., Annales D'Immunologie, "Suppression Et Traitement De L'uvéo–Rétinite Autoimmune Expérimentale Par Injections D'Extraits De Rétine," 129C 73–88 (1978).
Deibler, G.E. et al., "Large Scale Preparation of Myelin Basic Protein from Central Nervous Tissue of Several Mammalian Species," Prep. Biochem. 2:139–165 (1972).
Donoso, L.A. et al., "Human IRBP:Characterization of Uveitopathogenic Sites," Curr. Eye Res. 7:1087–1095 (1988).
Dorey, C. et al., "A Simple and Rapid Method for Isolation of Retinal S Antigen," Ophthalmic Res. 14:249–255 (1982).
Douglas, K. and Prince, C., "Eating Away at Disease," New Science pp. 36–40 (1995).
Gery, I. et al., "Retinal Specific Antigens and Immunopathogenic Processes They Provoke," N. Osborne and J. Chader (eds): Progress in Retinal Research, Oxford, Pergamon Press, vol. 5, pp. 75–109 (1986).
Gregerson, D.S. et al., "S–Antigen Specific Rat T Cell Lines Mediate EAU and EAP," Modern Trends in Immunology and Immunopathology of the Eye, Secchi, A.G., and I.A. Fregona (eds), Masson, Milan, pp. 20–25 (1989).
Gregerson, D.S. et al., "S–Antigen–Specific Rat T Cell Lines Recognize Peptide Fragments of S–Antigen and Mediate Experimental Autoimmune Uveoretinitis and Pinealitis," The Journal of Immunology 136:2875–2882 (1986).
Gregerson, D.S. et al., "Selection of Antibody Epitopes in an Immunopathogenic Neural Autoantigen," Journal of Neuroimmunology 24:191–206 (1989).
Gregerson, D.S. et al., "Identification of T Cell Recognition Sites in S–Antigen: Dissociation of Proliferative and Pathogenic Sites," Cellular Immunology 123:427–440 (1989).
Gregerson, D.S. et al., "Characterization of Immunologically Active Cyanogen Bromide Peptide Fragments of Bovine and Human Retinal S–Antigen," Exp. Eye Res. 43:803–818 (1986).

(List continued on next page.)

Primary Examiner—Lynette F. Smith
Attorney, Agent, or Firm—Darby & Darby

[57] ABSTRACT

The present invention provides a method of treating or preventing the clinical manifestation of an autoimmune disease having the symptoms of uveoretinitis in a mammal in need of such treatment comprising orally administering to said mammal an effective amount of an autoantigen, e.g., S antigen (S-Ag), and/or biologically active fragments, or analogs thereof specific for uveoretinitis.

Also provided is a pharmaceutical formulation useful for treating or preventing uveoretinitis in mammals comprising an effective amount of one or more of the foregoing autoantigen, fragments or analogs.

9 Claims, 9 Drawing Sheets

OTHER PUBLICATIONS

Gregerson, D.S. et al., "Preparation, Isolation, and Immunochemical Studies of the Cyanogen Bromide Peptides from a Retinal Photoreceptor Cell Autoantigen, S–Antigen," *The Journal of Immunology* 133:843–848 (1984).

Hafler, D.A., "Oligoclonal T Lymphocytes in the Cerebrospinal Fluid of Patients with Multiple Sclerosis," et al., *J. Exp. Med.* 167:1313–1322 (1988).

Higgins, P.J. and H.L. Weiner,"Suppression of Experimental Autoimmune Encephalomyelitis by Oral Administration of Myelin Basic Protein and Its Fragments," *J. Immunol.* 140:440–445 (1988).

Hirose, S. et al., "Lymphocyte Responses to Retinal–Specific Antigens in Uveitis Patients and Healthy Subjects," *Current Eye Research* 7:393–402 (1988).

Hirtenstein, A., "A Convenient Synthesis of Labelled Rhodopsin and Studies on its Active Site," *Biochem. J.*, 119:359–366 (1970).

Lider, et al., "Suppression of Experimental Autoimmune Encephalomyelitis by Oral Administration of Myelin Basic Protein," *J. Immunol.* 142:748–752 (1989).

Mokhtarian, "Adoptive Transfer of Myelin Basic Protein–Sensitized T Cells Produces Chronic Relapsing Demyelinating Disease in Mice," *Nature* 309:356–358 (1984).

Nussenblatt, R.B. and A.G. Palestine, "Cyclosporine:Immunology, Pharmacology and Therapeutic Uses," *Surv. Ophthalmol.* 31:159–169 (1986).

Nussenblatt, R.B. et al., "Cyclosporin A Inhibition of Experimental Autoimmune Uveitis in Lewis Rats," *J. Clin. Invest.* 67:1228–1231 (1981).

Nussenblatt, R.B. et al., "Cyclosporin A Therapy in the Treatment of Intraocular Inflammatory Disease Resistant to Systemic Corticosteroids and Cytotoxic Agents," *Am. J. Ophthalmol.* 96:275–282 (1983).

Nussenblatt, R.B. et al., "Local Cyclosporine Therapy for Experimental Autoimmune Uveitis in Rats," *Arch. Ophthalmol.* 103:1559–1562 (1985).

Nussenblatt, R.B. et al., "Cellular Immune Responsiveness of Uveitis Patients to Retinal S–Antigen," *Am. J. Ophthalmol.* 89:173–179 (1980).

Nussenblatt, R.B. et al., "Birdshot Retinochoroidopathy Associated with HLA–A29 Antigen and Immune Responsiveness to Retinal S–Antigen," *Am. J. Ophthalmol.* 94:147–158 (1982).

Nussenblatt, R.B. et al., "Inhibition of S–Antigen Induced Experimental Autoimmune Uveoretinitis by Oral Induction of Tolerance with S–Antigen," *J. of Immunol.* 144:1689–1695.

Nussenblatt, R.B. et al., "Treatment of Intraocular Inflammatory Disease with Cyclosporin A," *The Lancet* pp. 235–238, Jul. 30, 1983.

Oppenheim, J.J. et al., "Lymphocyte Transformations: Utilization of Automatic Harvesters," In Vitro Methods and Tumor Immunity, Bloom B.R., et al, *Eds, Acad. Press*, NY, pp. 573–585 (1976).

Redmond, T.M. et al., "Isolation and Characterization of Monkey Interphotoreceptor Retinoid–Binding Protein, a Unique Extracellular Matrix Component of the Retina," *Biochem.* 24:787–793 (1985).

Richman, L.K. et al., "Enterically Induced Immunologic Tolerance," *The Journal of Immunology,* 121:2429–2434 (1978).

Sanui, H. et al., "Identification of an Immunodominant and Highly Immunopathogenic Determinant in the Retinal Interphotoreceptor Retinoid–Binding Protein (IRBP)," *J. Exp. Med.* 169:1947–1960 (1989).

Sanui, H. et al., *Chem. Abstracts* 109:168702y, p. 572 (1988).

Sanui, H. et al., *Chem. Abstracts* 111:55593m, p. 579 (1989).

Sanui, H. et al., "Synthetic Peptides from IRBP Induce EAU and EAP in Lewis Rats," *Curr. Eye Research* 7:727–735 (1988).

Shields et al., "The Purification and Amino Acid Composition of Bovine Rhodopsin," *Biochem. Biophys. Acta* 147:238–251 (1967).

Shinohara, T. et al., "S–Antigen: Structure, Function and Experimental Autoimmune Uveitis (EAU)," *Progress in Retinal Research,* Osborne and Chader Eds. Pergamon Press, pp. 51–66.

Singh, V.K. et al., "Identification of a Uveitopathogenic and Lymphocyte Proliferation Site in Bovine S–Antigen," *Cellular Immunology* 115:413–419 (1988).

Wacker, W.B. et al., "Experimental Allergic Uveitis. Isolation, Characterization, and Localization of A Soluble Uveitopathogenic Antigen from Bovine Retina," *The Journal of Immunology* 119:1949–1958 (1977).

Wald, B., "The Synthesis of Rhodopsin from Retinene," *Proc. Natl. Acad. Sci. USA* 36:84–92 (1950).

Human S-Antigen:
```
MAASG KTSKS EPNHV IFKKI SRDKS VTIYL GNRDY IDHVS QVQPV DGVVL VDPDL
      ____Frag 1____
            ____Frag 2____
                  ____Frag 3____
                        ____Frag 4____
                              ____Frag 5____

VKGKK VYVTL TCAFR YGQED VDVIG LTFRR DLYFS RVQVY PPVGA ASTPT KLQES
__Frag 6_____
      _____ Frag 7 _____
            ____Frag 8____
                  ____Frag 9____
                        ____Frag 10____
                                      Frag
LLKKL GGNTY PFLLT FPDYL PCSVM LQPAP QDSGK SCGVD FEVKA FATDS TDAEE
11*_____=___
            ____Frag 13____
                  ____Frag 14____
                        _____ Frag 15 _____
                              _____ Frag 16 ___

DKIPK KSSVR YLIRS VQHAP LEMGP QPRAE ATWQF FMSDK PLHLA VSLNR EIYFH
__ Frag 17_____
      ____Frag 18____
            _____ Frag 19 _____
                  _____ Frag 20 _____
                        ____Frag 21____

VGEPIP VTVDV TNNTE KTVKK IKACV EQVAN VVLYS SDYYV KPVAM EEAQE KVPPN
Frag 22*____=_
      _____ Frag 23 _____
            ____Frag 24____
                  _____ Frag 25____
                        ____Frag 26____
                              ____Frag 27____
STLTK TLTLL PLLAN NRERR GIALD GKIKH EDTNL ASSTI IKEGI DRTVL GILVS YQIKV
__ Frag 28 _____
      _____ Frag 29 _____
            _____ Frag 30 _____
                  _____ Frag 31 _____
            _____ N Peptide _____
                        _____ M Peptide _____
                              _____ Frag 32 _____
                                    _____ Frag 33 ___

KLTVS GFLGE LTSSE VATEV PFRLM HPQPE DPAKE-- SIQDA NLVFE EFARH NLKDA
__ Frag 34 _____
      _____ Frag 35 _____
            _____ Frag 36 _____
                  _____ Frag 37 _____
                        _____ Frag 38 _____
                                          Frag
GEAEE GKRDK..NDA-DE        FIG. 8
39 _____
   _____ Frag 40 _____
```

FIG. 9A

```
S-Ag sequences:    Bovine
                   Human
                   Mouse 10        20        30        40        50
    MKANKPAPNHVIFKKISRDKSVTIYLGKRDYIDHVERVEPVDGVVLVDPE
MAASG TS SEPN       I         N   I       SQ Q         D
MAACG TN S---       V         K   V       SQ E         E 60        70        80        90       100
    LVKGKRVYVSLTCAFRYGQEDIDVMGLSFRRDLYFSQVQVFPPVGASGAT
       K   T         V I  T          R    Y        ASTP
       K   T         I M  T          R    Y        MSVL 110       120       130       140       150
    TRLQESLIKKLGANTYPFLLTFPDYLPCSVMLQPAPQDVGKSCGVDFEIK
       K   L   G                              S     V
       Q   I   A                              V     V 160       170       180       190       200
    AFATHSTDVEEDKIPKKSSVRLLIRKVQHAPRDMGPQPRAEASWQFFMSD
       TDS  A           Y    S       LE      R    T
       SDI  P           L    K       PE      S    S 210       220       230       240       250
    KPLRLAVSLSKEIYYHGEPIPVTVAVTNSTEKTVKKIKVLVEQVTNVVLY
       H A   NR    F        D   N E T      AC  VA
       H S   SK    F        T   N D V      VS  IA 260       270       280       290       300
    SSDYYIKTVAAEEAQEKVPPNSSLTKTLTLVPLLANNRERRGIALDGKIK
          V P  M   A    P     T    T L
          V P  S   T    Q     T    V V
                                    LLANNRERRGIALDGKIK
                                                Peptide N
                             SLTKTLTLVPLLANNRERRG
                                    Peptide   G2
```

FIG. 9B

```
         310        320        330        340        350
HEDTNLASSTIIKEGIDKTVMGILVSYQIKVKLTVSGLLGELTSSEVATE
             R    L         Q              F
             R    M         H              F
HE
Peptide N
   DTNLASSTIIKEGIDRTVLG
       Peptide M
            KEGIDKTVMGILVSYQIKVKL
              Peptide  G3
                                            TSSEVATE
                                              GM 360        370        380        390        400
VPFRLMHPQPEDPDTAKESFQDENFVFEEFARQNLKDAGEYKEEKTDQEAAMDE
              --     I  A  L       H     A   AE  G  R  KNDA-
              --     V  E  L       Q     T   NT  G  K  EDAGQ
VPFRLMHPQPED
      GM
```

METHOD OF TREATING OR PREVENTING AUTOIMMUNE UVEORETINITIS IN MAMMALS

This is a continuation of application Ser. No. 08/324,368, filed Oct. 17, 1994, which is a continuation of Ser. No. 08/178,461, filed Jan. 6, 1994 which was a continuation of Ser. No. 08/052,826 filed Apr. 23, 1993, which was a continuation of Ser. No. 07/928,881 filed Aug. 4, 1992, which was a continuation of Ser. No. 07/809,206 filed Dec. 13, 1991, which was a continuation of Ser. No. 07/551,632 filed Jul. 10, 1990, which was a continuation in part of Ser. No. 07/379,778 filed Jul. 14, 1989 all of which are abandoned.

FIELD OF THE INVENTION

The present invention provides a method of treating or preventing uveoretinitis in mammals. More particularly, this invention provides a method of treating or preventing the clinical manifestation of a disease having the symptoms of uveoretinitis comprising administering to a mammal in need of such treatment at least one uveoretinitis-suppressive agent selected from the group consisting of (i) autoantigens specific for uveoretinitis, (ii) fragments of such autoantigens possessing uveoretinitis-suppressive activity, and (iii) similarly active analogs of said autoantigens or fragments, in an amount effective to suppress or attenuate the clinical symptoms associated with said disease.

BACKGROUND OF THE INVENTION

The effective treatment of organ-specific inflammatory disorders of putative autoimmune origin is an ongoing goal in clinical medicine. To date, clinically oriented approaches have centered on the administration of pharmacologic substances that have a non-specific effect on the immune response. More recently, cyclosporine, an undecapeptide which suppresses immune response nonspecifically with respect to the antigen but which has a predominantly anti-T cell mode of action (Nussenblatt, R. B., and A. G. Palestine, Surv. Ophthalmol. 31:159, 1986) has been successfully used for the treatment of several disorders of presumed autoimmune origin, including uveitis (Nussenblatt R. B., et al., Am. J. Ophthalmol. 96:275, 1983). Unfortunately, cyclosporine has serious side effects which limit its usefulness. Furthermore, as with all present immunosuppressant therapies, the medication effects associated with cyclosporine are non-specific.

Experimental immuno-therapeutic approaches to suppression of autoimmune diseases including uveitis have focused on the manipulation of the immune response by non-pharmacologic means, such as monoclonal antibody therapy (Hafler D. A., et al., J. Immunol. 141:131, 1988); T-cell vaccination (Ben-Nun, A., et al., Nature 292:60, 1981); and the induction of immune tolerance by feeding of autoantigens. Recently, feeding myelin basic protein (MBP), or its fragments, has been shown to prevent the histological and clinical expression of experimental autoimmune encephalomyelitis (EAE), which has been used as a model for the human demyelinating disease, multiple sclerosis (Higgins, P. J., and H. L. Weiner, J. Immunol. 140:440, 1988; Lider, et al., J. Immunol. 142:748, 1989; Bitar, D. M., and C. C. Whitacre, Cell Immunol. 112:364, 1988).

Experimental autoimmune uveoretinitis (EAU) can be induced by several autoantigens derived from the retina (Gery, I., et al., in N. Osborne and J. Chader (eds): Progress in Retinal Research. Oxford, Pergamon Press, vol. 5, pp 75–109, 1986). To date, the most evaluated antigen and model system is that induced by the retinal S-antigen (S-Ag) (Gery, I., et al., in Progress in Retinal Research, supra). It is believed that S-Ag is involved in actual uveoretinitis in man because afflicted humans are sensitized to S-Ag. The S-Ag model shows EAU to be a T-cell mediated disorder, with administration of long-term CD4+ T-cell lines specific for S-Ag capable of inducing the disorder (Caspi R. R., et al., J. Immunol. 136:928, 1986).

The S-Ag EAU model is of particular interest for several reasons. First, to date, S-Ag is the only retinal autoantigen to which a substantial number of patients with endogenous intermediate and posterior uveitis consistently demonstrate in vitro proliferative responses (Nussenblatt, R. B., et al., Am. J. Ophthalmol. 89:173, 1980; Nussenblatt, et al., Am. J. Ophthalmol. 94:147, 1982). Second, the entire amino acid sequence of S-Ag has recently been reported, with two fragments designated N and M, respectively, demonstrating uveitogenicity (Donoso, L. A., et al., Curr. Eye Res. 8:1151, 1987; Singh, V. K., et al., Cell. Immunol. 115:413, 1988). Third, immune manipulation of this model appears to have excellent predictive value for the human uveoretinitis, as was demonstrated with the clinical effectiveness of cyclosporine use in humans (Nussenblatt, R. B., et al., J. Clin. Invest. 67:1228, 1981) which was first tested on the EAU model.

An important goal of the present invention is to provide a more specifically focused or directed therapy against uveitis. A more particular goal of this invention is to provide a method for suppressing the symptoms of uveoretinitis by oral or enteral administration of agents that are directed at diminishing the immune response to uveitis-specific antigens.

SUMMARY OF THE INVENTION

The present invention is directed to use of orally or enterally administered uveoretinitis-specific autoantigens and related substances to suppress or prevent the clinical manifestation of the disease. The invention also achieves induction of specific tolerance.

More particularly, the present inventors have discovered that symptoms associated with the autoimmune disease, uveoretinitis, can be suppressed or attenuated by orally administering to a mammal in need of such treatment or prevention, an effective amount of an autoantigen specific for uveoretinitis, uveoretinitis-suppressive fragments of such autoantigen or similarly active analogs of such autoantigen or fragments.

In addition, the present inventors have developed a pharmaceutical formulation comprising an effective amount of one or more of the foregoing uveoretinitis-suppressive agents. Such a formulation may be administered therapeutically or prophylactically to a mammal in need of such treatment or prevention.

BRIEF DESCRIPTION OF THE FIGURES

FIG. 8 is a diagram depicting the amino acid sequence of the human S-antigen polypeptide and the relative positions of polypeptides 3, 6, 8, 13, 18, 32, 35 and 36 of the present invention.

FIG. 9 is a diagram depicting the amino acid sequence of bovine, human and mouse S-antigen polypeptides and the relative positions of polypeptides GM, G2 and G3 of the present invention.

DETAILED DESCRIPTION OF THE INVENTION

Figure 1:
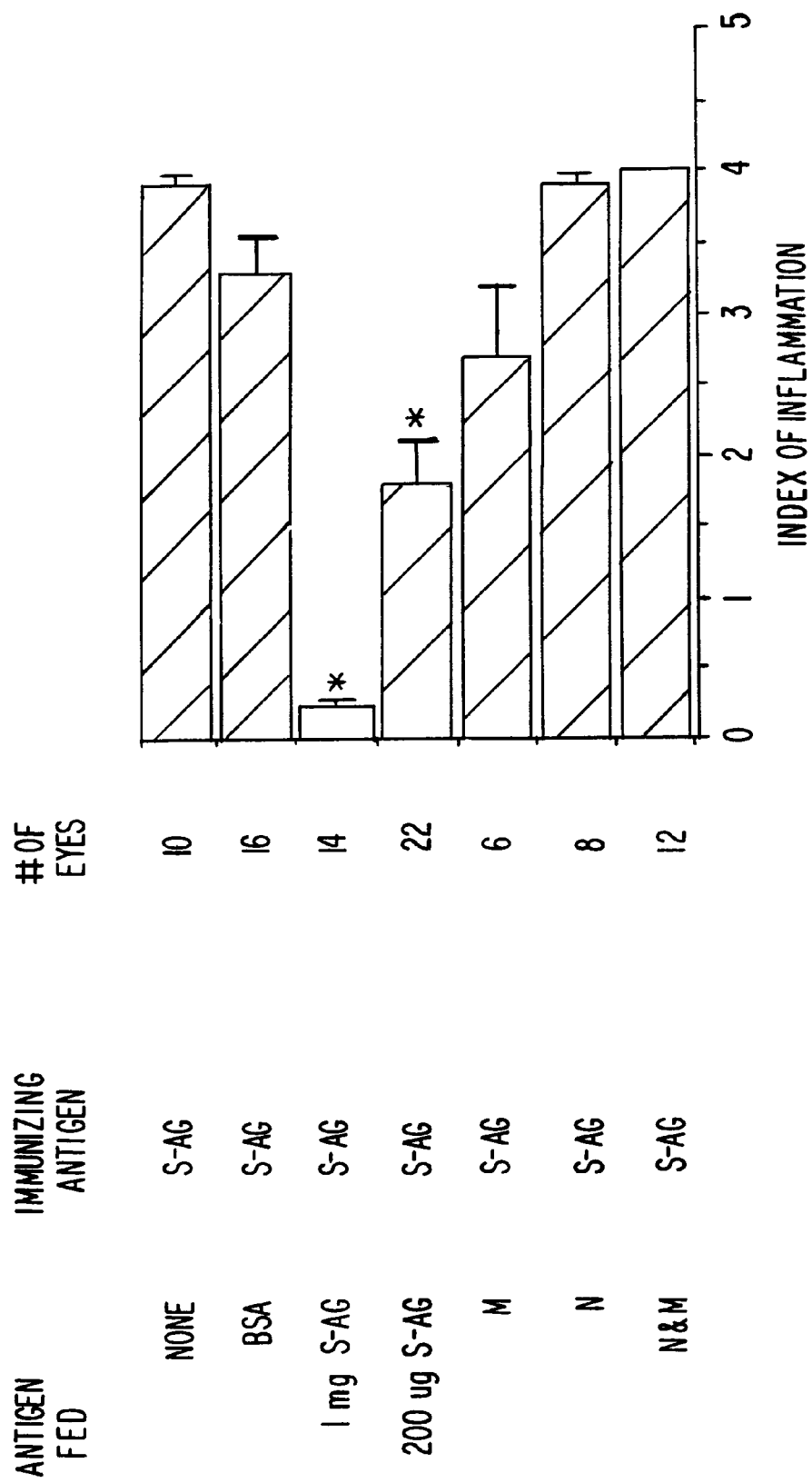
FIG. 1 depicts the degree of inflammation seen upon histologic examination in Lewis rat eyes 14 days after immunization with S-Ag. Asterisks indicate a statistically significant difference in inflammatory disease (EAU) as compared to rats that received no oral administration of S-Ag or fragment or rats which received an irrelevant antigen (bovine serum albumin, abbreviated BSA).

All literature references and patents cited in this specification are hereby incorporated by reference in their entirety.

Experimental autoimmune uveitis or uveoretinitis (hereinafter "EAU") is an autoimmune disease clinically characterized by a severe inflammation of the uveal tract, retina and anterior segment of the eye. There is characteristically destruction of retinal photoreceptor cells. All of these findings can be observed in human cases of uveitis. Apinealitis has been concomitantly seen in lower animals and non-human primates with EAU.

The present invention provides a method for treating or preventing a disease presenting the clinical symptoms of uveoretinitis in a mammal (including primates, such as humans) comprising orally administering to the mammal in need of such treatment, or for prevention of the disease, an amount of an autoantigen specific for uveoretinitis, a uveitis-suppressive fragment of such antigen, an analog of such antigen or fragment such analog having uveitis-suppressive activity, the amount administered being effective to suppress or attenuate clinical symptoms associated with said uveoretinitis.

As used herein, "autoantigen" is any substance normally found within a mammal which, in an abnormal situation, is no longer recognized as part of the mammal itself by the lymphocytes or antibodies of that mammal, and is therefore attacked by the immunoregulatory system as though it were a foreign substance. The term also includes antigenic substances which induce conditions having the symptoms of an autoimmune disease when administered to mammals. An autoantigen specific for uveitis is a substance within the foregoing definition which (a) is subject to attack by the immune system of a mammal having uveitis; and/or (b) induces a disease with the symptoms of uveitis upon parenteral administration in a mammal.

The term uveitis-suppressive agent shall include autoantigens specific for uveitis as well as fragments or analogs thereof having the property of suppressing the symptoms of uveitis upon oral or enteral administration, preferably without substantially affecting the general ability of the mammal so treated to mount an immune response against antigens.

Autoantigens within the scope of the present invention include the S-antigen (hereinafter "S-Ag") which is a soluble photoreceptor cell protein having an apparent molecular weight of about 48 kilodaltons (kDa). S-Ag may be prepared by isolating and purifying it from mammalian eyes, e.g., bovine eyes, using techniques well-known in the art such as the method described in Dorey, C., et al, *Ophthalmic Res.* 14:249–255, 1982. S-Ag has been found in all mammalian eyes to date, but bovine eyes are the preferred source because of ready accessibility and similarity to the human S-Ag.

Briefly, the S-Ag can be isolated and purified from bovine retinas by ion-exchange chromatography or by isoelectric focusing. Alternatively, S-Ag can be rapidly isolated and purified by salt precipitation, e.g., using a first 50% ammonium sulfate precipitation and a second 50% ammonium sulfate precipitation, gel filtration, e.g., Sephadex G-200 (Pharmacia Inc., Piscataway, N.J.) filtration, and final purification by adsorption chromatography on hydroxylapatiteagarose, e.g., HA-Ultrogel® (available from Pharmindustrie, France) chromatography, all of which is described by Dorey, et al., supra. S-Ag represents approximately 3% of the proteins present in the crude retinal tissue extract. By isolating and purifying using the sequential steps of precipitation, filtration and adsorption chromatography, about 40% of S-Ag is typically recovered after the final chromatographic separation, as measured for example by the radial immunodiffusion test. Minor contaminants can be removed by high pressure liquid chromatography (HPLC) if desired. Alternatively, S-Ag can be purified by following the method described by Wacker, W. B., et al., *J. Immunol.* 119:1949–1958. Dorey et al.'s method appears to provide best results among all methods to date.

The complete amino acid sequence of bovine, human and mouse S-Ag has been published in Shinohara, T., et al., *S-Antigen: Structure, Function and Experimental Autoimmune Uveitis (EAU)* in *Progress in Retinal Research,* Osborne and Chader Eds. Pergamon Press, pp. 51–66. A partial sequence of S-Ag has also been published by Donoso, C., et al., supra.

In addition to "complete" or whole autoantigens, such as S-Ag, fragments which are capable of suppressing uveitis symptoms (including such symptoms as are induced by the complete autoantigen or a fragment thereof) and similarly active analogs derived therefrom, may also be orally or enterally (e.g., by tube feeding) administered in accordance with the present invention. Among S-Ag fragments which may be so administered are N and M antigens. Other suitable S-Ag fragments are the noninducing fragments disclosed in Donoso, et al, supra, 1987. Other ocular antigens such as Interphotoreceptor Retinoid-Binding Protein (IRBP) and rhodopsin can also be used as uveitis-specific autoantigens. IRBP has been isolated from monkey interphotoreceptor matrix (IPM) and characterized in terms of isoelectric focusing band patterns, carbohydrate analysis, ultracentrifugal concentration distribution, amino acid analysis, amino-terminal analysis, spectral properties, e.g., tryptophan and sulfhydryl content and fluorescence studies. (Redmond, T. M., et al., *Biochem.* 24:787, 1985). Rhodopsin has also been well described and characterized by Shields et al., *Biochem. Biophys. Acta* 147:238, 1967; Wald, Brown, *Proc. Natl. Acad. Sci.* USA 36:84, 1950; and Hirtenstein, A., *Biochem. J.* 119:359, 1970.

The term "analogs" as used herein encompasses substances that differ from autoantigens or fragments by the deletion, addition or substitution of one or more amino acids, moieties or substituents but are so structurally related to the uveitis-suppressive agents as to have the same type (but not necessarily the same degree) of suppressive activity when orally or enterally administered. Fragments and analogs can be synthesized using conventional chemical synthetic techniques, e.g. by using the well-known Merrifield peptide synthesis technique described, for example, in Merrifield, R. B. *Fed. Proc. Am. Soc. Ex. Biol.* 21:412, 1962 and *J. Am. Chem.Soc.* 85:2149, 1963; and Mitchel, A. R. *J. Am. Chem.Soc.* 98:7357, 1976. Analogs can be constructed for example by identifying an equivalent amino acid sequence (Tam., J., et al.) *J. Am. Chem. Soc.,* 105:6442, 1983; and using one of the general peptide synthesis methods referred to above or disclosed elsewhere herein. Alternatively, S-Ag and suppressive fragments or analogs can be prepared using recombinant DNA techniques according to methods well-known in the art.

The methods and pharmaceutical formulations of the present invention, the latter to be described shortly, include the use of natural and synthetic autoantigens, e.g., S-Ag, and fragments and analogs thereof as well as genetically engineered autoantigens, fragments, and analogs.

It has been widely reported that EAU pathogenesis is T-cell mediated. Without wishing to be bound by any particular theory, the present inventors believe that oral administration or feeding of autoantigenic proteins, e.g., the autoantigen and fragments or analogs thereof specific for uveoretinitis, induces antigen-specific suppression through CD8+ T– cells (suppressor cells) that are elicited through such feeding. These cells mediate the suppression (down-regulation) of the immune response. This down-regulation permits suppression of clinical symptoms (such as inflammation) associated with an autoimmune disease, e.g. EAU, having the symptoms of uveitis.

The present invention illustrates that oral or enteral administration of the whole S-antigen molecule will lead to immune tolerance and the prevention of S-Ag-induced EAU. Further, antigen specific suppression of the immune response has been demonstrated in vitro, and T-suppressor involvement has been confirmed by the fact that anti-CD8 antibody (which is specifically directed to the CD8 suppressor/cytotoxic marker on the surface of lymphoid cells) blocks this immune response suppression.

T-suppressor-mediated immune suppression is illustrated in Example 3 below in which non-immunized mammals, e.g., rats, are fed defined quantities of S-Ag three times with feedings separated by 2–3 days. Thereafter spleen cells from the animals are collected and irradiated. A responder cell, e.g., a CD4+, S-Ag-specific T-helper line (ThS-Ag) or a CD4+ PPD-specific T-helper line (ThPPD) were cultured in the presence of the irradiated spleen cells. Antigen-driven indicator cell proliferation was then measured in the presence or absence of appropriate antibodies, such as OX-8 antibody which recognizes CD8 (a glycoprotein specifically present on the surface of a subset of rat T suppressor cells) and Leu 2a (an unrelated antibody which has no known affinity to rat T cell subsets). One or more of these antibodies were added to some of the aforementioned cultures. The cell proliferation results from these cultures indicate that profound (and statistically significant) suppression of the T-helper ThS-Ag line is specifically obtained by the oral feeding of an autoantigen such as S-Ag in accordance with this invention. In turn, this indicates that the suppression is mediated by antigen-specific (e.g., S-Ag-specific) suppressor cells which are present in the spleen-cell population of the S-Ag-fed rats.

(S-Ag)-induced EAU is an experimental model for human uveitis of considerable predictive value for the human disorder. In rats, EAU can be induced by direct immunization with S-Ag or by the transfer of CD4+/CD9– T lymphocyte lines to naive hosts, Gery, I. M., et al, supra; Caspi R. R., et al., supra. The dominant role of the T cell in this disorder is further supported by the observation that cyclosporine (which has a predominantly anti-T-cell mode of action) can effectively prevent EAU (Nussenblatt, R. B., et al., 1981, supra). The results disclosed herein indicate that orally-induced immune tolerance has applicability in many organ-specific autoimmune models, particularly those with a predominant T-cell role. However, this is not to say that the oral tolerance approach can or should be tried blindly. For example, the effects of antigen feeding noted in EAU do not totally parallel those seen in the EAE/MBP model. While both inducing and noninducing fragments of MBP were capable of inducing an immunotolerant state against EAE, two inducing fragments of the S-Ag were not capable of doing so for S-Ag-induced EAU. Recently, the N and M fragments of the S-Ag molecule have been reported as being uveitogenic (Donoso, L. A., et al., supra; Singh, V. K., supra). These fragments (even when fed together) failed to induce an immunotolerant state against whole S-Ag although the M-fragment-induced substantial immunotolerance against EAU in turn induced with M-fragment or N-fragment. In addition, noninducing fragments of S-Ag are expected to have EAU-suppressive activity. For example, fragments selected among those mentioned in Donoso, supra can be synthesized and tested for ability to induce tolerance in accordance with the methodology illustrated below with, optionally, adjustment of the amounts administered as is well-known in the art.

The EAU disease induced with the M- and N-fragments was not as severe as that caused by the native molecule, and the molar amount of each fragment needed to induce disease was several fold higher than the minimum EAU-inducing amount of S-Ag of 1–5 ug. As stated above, oral feeding with either the M fragment (or whole S-Ag) did protect animals against either N- or M-induced EAU. Thus, this orally-induced tolerant state shows strict antigen specificity which is further supported by the observation that feeding with S-Ag did not prevent the expression of the unrelated autoimmune disorder EAE, induced by the unrelated autoantigen MBP. In view of these findings, incorporation of discrete fragments of S-Ag in oral or enteral pharmaceutical formulations constitutes a useful adjunct of (or substitute for) S-Ag therapy in accordance with the present invention: S-Ag fragments that elicit T-suppressor cells specific for S-Ag are clearly useful and S-Ag fragments that protect against challenge with the same (or a different) S-Ag fragment would also be useful as adjuncts to uveitis therapy since uveitis symptoms may be caused by more than one autoantigen including autoantigens identical or homologous to fragments of S-Ag.

The in vitro suppression of immune response evidenced by a statistically significant (hereafter sometimes referred to as "substantial") decrease in the proliferative response of lymph node cells from animals fed S-Ag and particularly by the suppression of indicator ThS-Ag cells (which are specific to S-Ag but of the T-helper type) with splenocytes from S-Ag-fed animals confirms that antigen-specific suppression involving T-cells is being induced by oral feeding. The finding described in Example 3 that the OX-8 antibody, which recognizes CD8 (a T-suppressor-specific glycoprotein on the surface of a subset of rat T suppressor cells), reversed the suppression indicates that T-suppressor cells are responsible for the observed inhibition.

Thus, the present invention is directed to a method for suppressing the clinical manifestation of an autoimmune disease having the symptoms of uveoretinitis in a mammal in need of such treatment, comprising orally and enterally administering to the mammal an effective amount of an uveitis-suppressive agent selected from the group consisting of (i) an autoantigen; (ii) a fragment of said autoantigen which when orally administered to a mammal suppresses the symptoms of EAU-induced with said autoantigen or a fragment thereof; (iii) an analog of said autoantigen or fragment having uveitis-suppressive activity; and (iv) combinations of any or all of the foregoing.

The term "suppression" is intended to include prevention of said clinical manifestations or symptoms, as well as complete elimination or at least measurable attenuation of such manifestations and symptoms. To be an "effective amount" the amount of said uveitis-suppressive agent should be sufficient to cause a measurable and preferably a statistically significant attenuation of at least one clinical symptom associated with uveitis, e.g. inflammation, decrease in visual acuity, and/or cystoid macular edema or any other parameter, the alteration of which from a normal value is associated with uveitis.

In general terms, an effective amount of the uveitis suppressant agent for suppressing or attenuating clinical symptoms of uveitis in mammals comprises from about 0.4 to about 15 mg/kg/day. In man, such an effective amount of the uveitis suppressant agent comprises from about 0.1 to about 15 mg/kg/day, preferably from about 4 to about 8.5 mg/kg/day. In other words, for a 70 kg adult, the effective amount is from about 30 to about 1000 mg/day, preferably from about 300 to about 600 mg/day. For rodents, the effective amount of the uveitis suppressant agent comprises from about 100 ug to about 10 mg per rodent. Of course, the broad ranges given above may need to be adjusted according to factors such as the age, sex and physical condition of the subject to be treated, the severity of the disease, and the specific suppressive activity of the agent or agents to be administered. However, such refinement of suitable dosages can be determined by persons of ordinary skill in the field using no more than routine experimentation. For example, optimum dosage can be established using serially diluted preparations of the active agents of the present invention in connection with a suitable testing procedure such as that described in the examples below. Alternatively, a matrix of dosages and frequency of administration can be established and groups of experimental subjects can be assigned to each point on the matrix in order to determine the optimum conditions.

The effective amounts of autoantigen (or fragments, or analogs) is administered orally or enterally in accordance with this invention. The autoantigen, e.g., S-Ag and fragments, is desirably administered alone, or in a physiologically acceptable buffer such as phosphate buffered saline (PBS).

Such effective amounts can be dispensed to a mammal in need of treatment in one daily oral dose or in two or more divided daily oral doses. In man, such divided daily oral doses may comprise, preferably, 3 times/day over a period of from about 90 to about 120 days, or even longer to insure sufficient uptake and absorption of the autoantigen, fragment or analog. Treatment may continue or be resumed if symptoms persist or recur.

The present invention also provides pharmaceutical formulations and effective dosage forms comprising an effective amount for oral or enteral administration of an autoantigen specific for uveoretinitis and/or uveitis-suppressive fragments or analogs thereof, and a pharmaceutically acceptable carrier or diluent.

The terms defined above are equally applicable to such pharmaceutical formulations. Thus, for example, the autoantigen may comprise the S-antigen (S-Ag) or biologically active fragments thereof.

The pharmaceutical formulation provided by this invention may be in solid, semisolid or liquid form and may further include pharmaceutically acceptable fillers, carriers or diluents, and other inert ingredients as well as adjuvants. Examples of such additional ingredients include: phosphate buffered saline (PBS), starch, sugar, and bentonite and silica. It may also be mixed with other suitable food forms, flavor-enhancers and the like. Oral formulations may be in the form of capsules, tablets or caplets optionally coated with an inert coating (including a coating that facilitates ingestion) or may be incorporated in sustained release oral or enteral drug-delivery systems as are well-known in the art. Nonlimiting examples of such coatings include cellulose, gelatin or derivatives of either. Liquid formulations which are also contemplated could be administered in liquid form or could be encapsulated. Gel formulations are also contemplated.

The pharmaceutical formulations of the present invention are useful to treat or prevent the clinical manifestations of autoimmune diseases having the symptoms of uveitis in mammals, including primates, such as man.

The present invention is described below in specific working examples which are intended to illustrate the invention without limiting its scope.

MATERIALS AND METHODS

Animals

Female Lewis rats weighing 180–200 grams were obtained from Charles River Laboratories (Raleigh, N.C.), and were used in all experiments.

Antigens and Immunization Scheme

The retinal antigen S-Ag was purified from bovine retinas. (Dorey, C., et al., *Ophthalmic Res.* 14:249, 1982). The two uveitogenic S-Ag fragments, the N and M, (Donoso, L. A., et al., supra; Singh, V. K., supra) were used. The S-Ag fragments were produced synthetically according to the manufacturer's instructions (user bulletin), using a DNA Synthesizer Model 380/381, Applied Biosystems, Foster City, Calif.) Alternatively, the peptides can be synthesized according to other known techniques, e.g., as described in Donoso, 1987, supra, or in the Merrifield and/or Mitchel also cited above. Both fragments were 18 amino acids in length: The M peptide had the amino acid sequence DTNLASSTI-IKEGIDKTV and the N peptide had the sequence VPLLAN-NRERRGIALDGKIKHE (wherein: A=alanine, C=cysteine; D=aspartic acid; E=glutamic acid; F=phenylalanine; G=glycine; H=histidine; I=isoleucine; K=lysine; L=leucine; M=methionine; N=asparagine; P=proline; Q=glutamine; R=arginine; S=serine; T=threonine; V=valine; W=tryptophan; and Y=tyrosine).

Guinea pig myelin basic protein (MBP) was purified from brain tissue by the method of Diebler et al. (Diebler, G. E., et al., *Prep. Biochem.* 2:139, 1972).

All immunizations were carried out using 50 micrograms of the antigen emulsified in complete Freund's adjuvant (CFA; Difco, Detroit Mich.), which was augmented with *M. tuberculosis* strain 37RA which are dead bacteria for the adjuvant (DIFCO, Detroit, Mich.) to reach a final concentration of 2.5 mg/ml. Animals were injected with 0.1 ml of emulsion into only one hind footpad. All animals were observed for 14 days after the immunization, at which time the animals were sacrificed. Their eyes were removed, placed in 10% formaldehyde, and slides stained with hematoxylin and eosin were prepared. The slides were evaluated histologically for inflammation by one of the investigators who served as a masked observer, using the criteria reported in Nussenblatt, R. B., et al., *Arch. Ophthalmol.* 103:1559, 1985. These criteria represent a modification of the grading system described by Wacker et al. (Wacker, W. B., et al., *J. Immunol.* 119:1949 (1977) which was for guinea pigs. Briefly, the grading criteria for the evaluation of posterior segment disease in the rat is as follows:

0, no evidence of inflammatory disease; trace (0.5+), architecture of retina grossly intact. Areas of focal destruction were 1+, focal areas of destruction with marked dropout of photoreceptors; 2+, small exudative retinal detachment with larger destruction, mild to moderate number of cells in vitreous; 3+, retinal architecture beginning to be lost, larger exudative retinal detachment, moderate to large number of cells in vitreous; and 4+, total destruction of retinal architecture.

For those animals immunized with MBP, EAE was characterized by limb paralysis and scored as follows: 0—no disease; 1—decreased activity, limp tail; 2—mild paralysis, unsteady gait; 3—moderate paraparesis, limbs splayed apart; and 4—tetraplegia. All other materials used are available commercially.

EXAMPLE 1

Oral Tolerance: Protection Induced Through Oral Feeding

Rats were fed three times with either 200 micrograms of S-Ag (total 600 micrograms) or 1 mg (total 3 mg) of S-Ag, or with 1 mg (total 3 mg) bovine serum albumin (BSA), or 200 micrograms each (total 600 micrograms) of the N and/or M fragment(s), on day-7, day-5, and day-2. Immunization as described above was performed on day zero. Animals receiving MBP orally were given 1 mg of the protein four times, with the additional feeding given on day-9. All the antigens were given in 1 ml PBS using a 23 gauge needle covered with plastic tubing.

Figure 2:
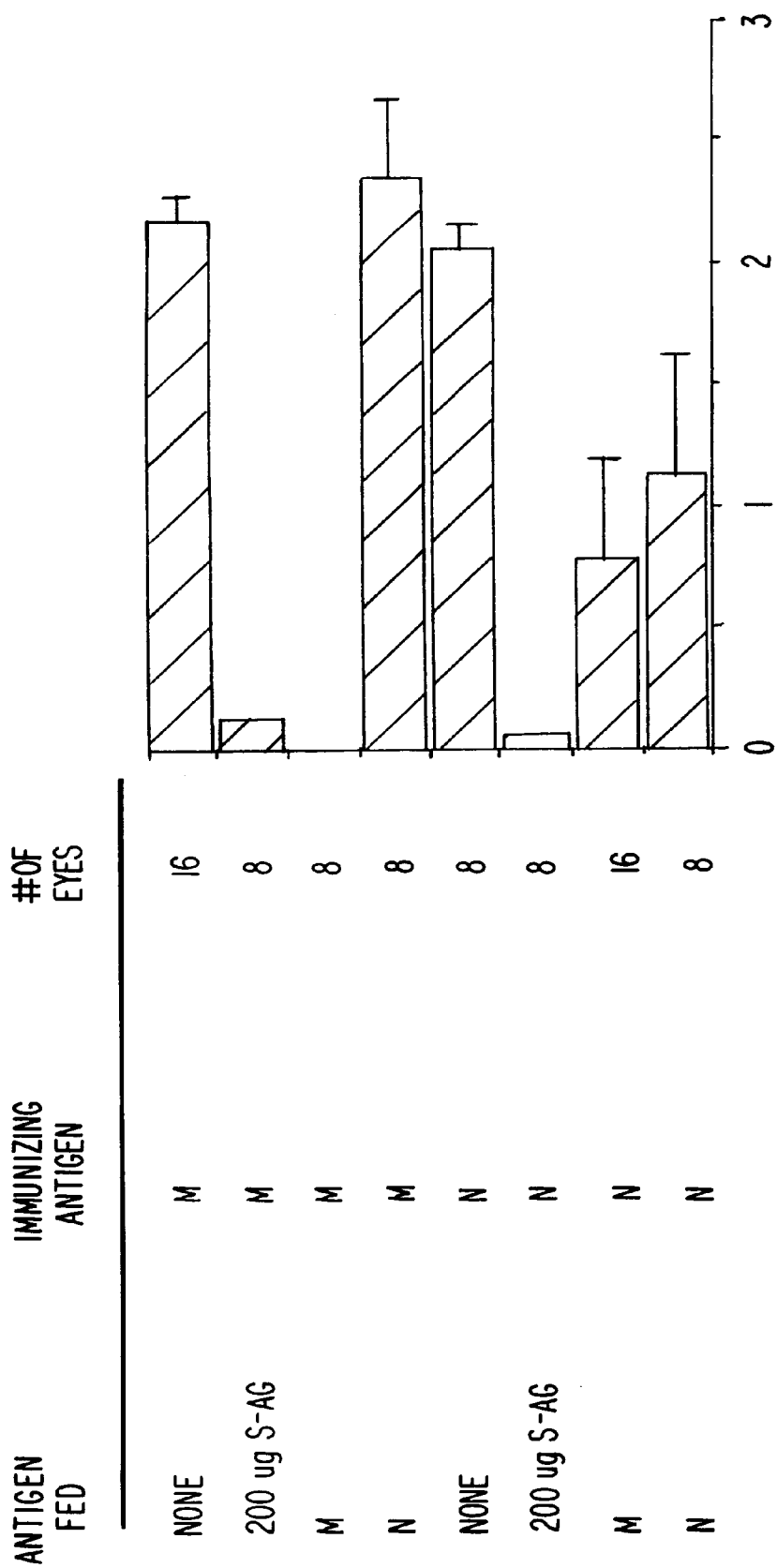
FIG. 2 depicts the degree of inflammation seen histologically in eyes of Lewis rats fed with S-Ag or a fragment 14 days after immunization with either the M or N fragments of the S-Ag.

Unfed control animals immunized with the uveitogenic protein (S-Ag), and its M and N fragments, developed disease between 11–14 days after challenge. As can be seen in FIGS. 1 and 2, the degree of ocular inflammation as read histologically by the masked observer varied to some degree depending on the immunizing antigen, with the whole S-Ag molecule inducing the most severe disease. FIG. 1 shows the inflammatory disease present on histologic examination of eyes immunized with S-Ag and fed with various antigens. A severe inflammatory response was noted in the eyes of animals that did not receive any feeding, as well as in animals fed a total of 3 mg of bovine serum albumin. However, when animals were fed with S-Ag, a statistically significant (substantial) reduction in inflammatory disease was noted. Even when animals were fed a total of 0.6 mg of S-Ag in three divided doses, the inflammatory response was statistically significantly decreased as compared to that observed after feeding with 0.6 mg of BSA (Wilcoxon ranked sum test described in Colton, T., Little Brown, 1974, pp. 219–221; p=0.003). An even more dramatic decrease in inflammatory disease was noted when animals were fed a total of 3 mg of S-Ag compared to feeding with 0.6 mg BSA (Wilcoxon ranked sum test, p=0.003), with only 2 of 14 eyes showing any inflammatory response upon histologic examination.

The N and M fragments of the S-Ag were also fed to animals to evaluate their capacity to prevent disease. When animals were fed a total of 0.6 mg of each of the N and M fractions (an excess of 20 times of S-Ag that was fed on a molar basis), neither the M nor the N fragment was capable of diminishing S-Ag-induced disease in a statistically significant manner; the effect was comparable to that of feeding with BSA. In fact, when animals were fed both fragments simultaneously, receiving a total of 0.6 mg of each, the ocular disease noted was similar to or slightly greater than that seen with feeding a non-ocular antigen, BSA.

FIG. 2 shows the effect of feeding various antigens on experimental uveitis induced by the N and M peptides of S-Ag (autologous induction and oral suppression). Feeding with whole S-Ag (a total of 0.6 mg) was capable of preventing uveitis in animals immunized with either the N fragment (7/8 eyes), or the M fragment (6/8 eyes). The N fragment (at a total oral dose of 0.6 mg) was not as effective in preventing N fragment-induced disease as the S-Ag was, while the M fragment given at the same oral dosage did effectively prevent M fragment-induced uveitis and, to a degree, also N-fragment-induced disease. Feeding the N fragment to animals had no effect on M fragment-induced disease. These results indicate that at least the M-fragment and possibly also the N-fragment would be useful as adjuncts to oral whole S-Ag therapy.

In a separate set of experiments, feeding with the S-Ag was tested to determine the effects on the development of MBP-induced EAE. Three animals treated with a total of 3 mg of S-Ag orally and immunized with MBP developed severe EAE (average score 3.66), while none of the animals given MBP orally before immunization with that antigen developed any signs of EAE (data not shown). Therefore, the oral (or enteral) administration of S-Ag gives specific protection and does not attenuate the recipient's ability to mount an immune response against unrelated autoantigens.

EXAMPLE 2

In Vitro Proliferative Responses

Fourteen days after immunization, animals were sacrificed and the draining popliteal lymph nodes were removed, teased and prepared for culture according to Oppenheim, J. J., et al, 1976, *Lymphocyte transformations: Utilization of Automatic Harvesters* in *In Vitro Methods and Tumor Immunity*, Bloom B. R., et al, Eds, Acad. Press, NY, pp. 573–585. In brief, cell cultures were established at a concentration of $1.5 \times 10^6$ cells/ml in flat-bottomed microtiter wells containing 0.2 ml of CRPMI, (RPMI 1640 medium from Gibco, Grand Island, N.Y.) supplemented with 100 ug/ml penicillin, 100 ug/ml streptomycin, 50 ug/ml glutamycin, 2 mM glutamine, 1 mM sodium pyruvate, 0.1 mM nonessential amino acids, $5 \times 10^{-5}$ M 2-mercaptoethanol as described (Caspi R. R., supra) and containing 1.5% rat serum. All cultures were performed either in triplicate or in sextuplicate. The concentration of S-Ag and the fragments N and M were 25 micrograms/ml, while Con A was used at 10 micrograms/ml. Cultures were incubated at 37° C. in 5% carbon dioxide. Pulsing with 1 microCurie/well of tritiated thymidine was performed 14 hours before the termination of the culture (4 days after initiation), and cells were harvested on a Mash II harvester (Cambridge Technology, Cambridge, Mass.). The results are presented as stimulation index, which was defined as the counts in the antigen-containing wells and are reported as the mean±standard-error-of-mean (SEM). For this group, a stimulation index of 2.5 or more was regarded as evidence of an in vitro "anamnestic" cellular response. A stimulation index of 2.5 or more is the customary standard and represents more than 2 times (2×) the standard deviation of the mean.

Figure 3A:
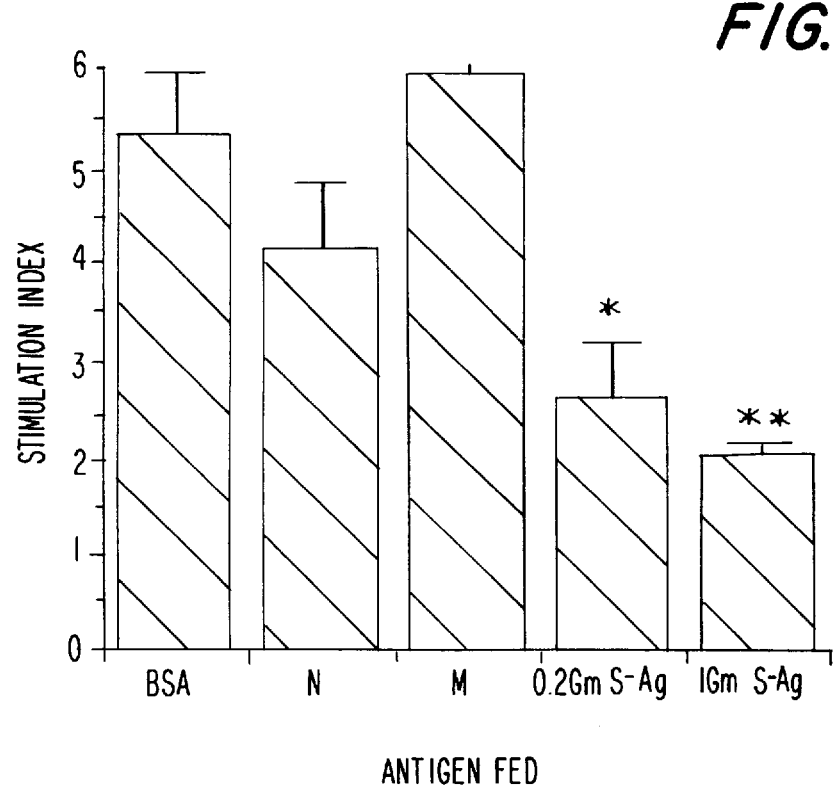
FIG. 3A shows the effect of oral administration of S-Ag, N fragment, M fragment and BSA on the proliferative responses to S-Ag measured in lymph node cells draining the site of S-Ag immunization. Results are of at least four animals and are presented as Stimulation Index ±S.E.. The single asterisk indicates a statistically significant difference (p=0.018) when compared to oral administration of BSA while the double asterisk indicates a p value of 0.005.

The effect of feeding various antigens on the proliferative response to S-Ag in animals immunized with this antigen can be seen in FIG. 3A. The cultures from at least four animals are represented for each column. As can be seen, the proliferative responses to the S-Ag after feeding with either the N or M fragment are not statistically different from those seen after feeding with BSA (Students' test, described in T. Colton, pp. 129–131, supra; p=0.259 and 0.803 respectively). Hence, in these animals, clinical protection to whole-autoantigen-induced disease was not obtained by feeding the fragments. When 0.2 mg of S-Ag was given three times, a decrease in the proliferative response could be noted, which was statistically significant (as opposed to that seen with BSA feeding (p=0.018)) and which correlated with the partial protection of these animals from EAU. However, the most impressive decrease (p=0.005) in in vitro proliferative responses was noted after feeding with 1 mg of S-Ag given three times before immunization. This was the oral dosage which is yielded the best protection against the clinical expression of EAU-induced by S-Ag immunization.

Figure 3B:
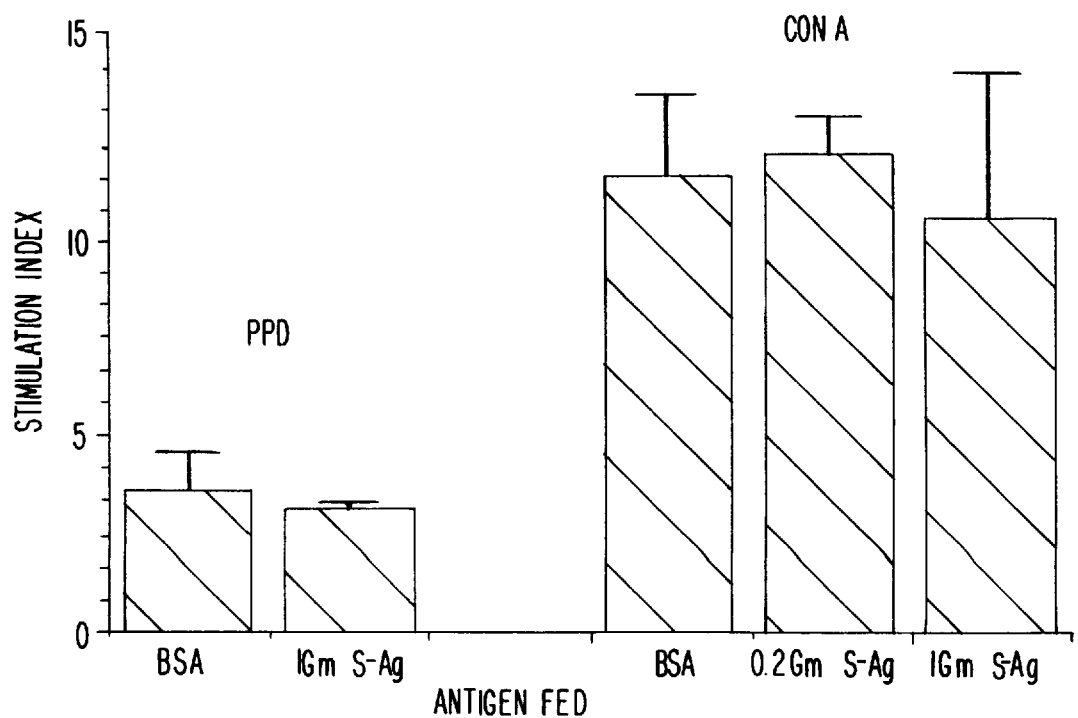
FIG. 3B shows the effect of oral administration of BSA and S-Ag on the proliferative responses to unrelated antigens PPD (purified protein derivative of tuberculin) and Con A (Concanavalin A) measured in lymph node cells draining the site of S-Ag immunization.

FIG. 3B shows the proliferative responses to PPD, an integral component of the complete Freund's adjuvant (Difco, Detroit, Mich.) used in the immunization, and to the mitogen Con A. (Sigma, St. Louis, Mo.). No statistically significant differences could be elicited between the animals receiving oral feedings of BSA or S-Ag.

The results demonstrate that the protection against clinical expression of uveitis symptoms by oral administration of autoantigen is specific to the antigen administered orally, furthermore, such protection is T-cell mediated (at least in part) and dose-dependent.

EXAMPLE 3

In Vitro Suppression of Proliferative Responses to Antigen and Mitogen

Non-immunized rats were fed either 1 mg of S-Ag, bovine serum albumin (BSA), or the adjuvant KLH, or saline three times, separated by 2–3 days, with spleen cells collected four days after the last feeding. The splenocytes ($2 \times 10^6$ cells/ml) were then placed in CRPMI augmented with 10% fetal bovine serum, pulsed with 5 micrograms/ml of S-Ag or 2 micrograms/ml Con A, and incubated for 48 hours. The cells from these cultures were used as modulator cells and designated as Tm Control if they were derived from saline-fed animals, TmKLH if from KLH-fed animals, TmBSA if from BSA-fed animals, and TmS-Ag if they were derived from S-Ag-fed animals.

A CD4+, S-Ag specific T-helper line (ThS-Ag), known to induce EAU on adoptive transfer, (according to the method of Mokhtarian, *Nature*, 309:356 (1984)) was used as a responder cell in all experiments. In parallel experiments, a CD4+/PPD– specific T-helper line (ThPPD) was also used (Caspi et al., supra). $2 \times 10^4$ responder cells were cultured with $5 \times 10^5$ irradiated (1500 rads) Lewis rat thymocytes, which served as antigen-presenting cells (APC). To some cultures, different numbers of irradiated (1500 rads) Tm Control, TmBSA, TmKLH or TMS-Ag modulator cells were added. All cultures were established in triplicate in CRPMI with 1.5% rat serum in flat-bottomed 96 well plates (Costar), with some wells stimulated with a 10 microliter aliquot of S-Ag (25 micrograms/ml final concentration), or Con A (2 micrograms/ml final concentration), or with medium alone. Cultures were incubated for 3 days, with the pulsing of 1 microCurie/well of tritiated thymidine performed 14 hours before the termination of the culture. Cells were harvested on a Mash II harvester.

To some of the wells containing the ThS-Ag, APC, and TmS-Ag, either the OX8 antibody (which specifically recognizes the suppressor/cytotoxic subset of rat T cells) (Sera Lab, Westbury N.Y.) or the Leu 2a antibody (which has no known affinity to rat T cell subsets) (Becton Dickinson, Mountain View Calif.) was added at the initiation of the cultures.

Figure 4A:
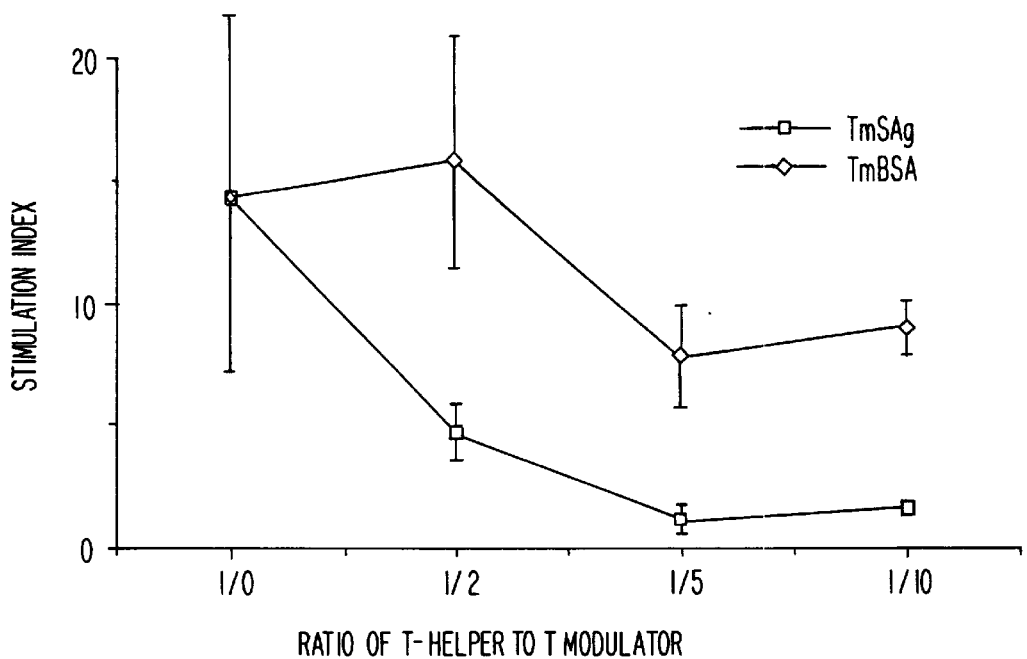
FIG. 4A shows the effect on the S-antigen specific indicator cell line ThS (ThS-Ag) of exposure to splenocytes from either S-Ag- (TmSAg) or BSA- (TmBSA) fed animals preincubated in vitro with S-Ag. A suppression of the ThSAg response to S-Ag can be seen at all ratios of ThSAg to TmSAg and this degree of suppression was statistically significantly higher at ratios of 1:5 and 1:10 (p=0.04 and 0.002) when compared to the responses seen with ThSAg and TmBSA co-cultures.

After an in vitro pre-incubation with either S-Ag or Con A, co-cultures of splenocytes from either S-Ag or BSA-fed animals and an S-Ag CD4+T cell line (ThS-Ag) were performed. The results of these experiments can be seen in FIG. 4. The degree of suppression of antigen-driven proliferation of the indicator ThS-Ag can be seen. FIG. 4A shows the suppression obtained after pre-incubating in vitro TmS-Ag or Tm-BSA with S-Ag. A profound suppression of the ThS-Ag response to S-Ag was obtained at all ratios of T-helper to splenocyte cell combinations tested, with the suppression of the proliferative response approaching that of background in the cultures containing one ThS-Ag to five or ten Tm-SAg. The pattern of suppression noted with the addition of Tm-BSA was different, with no suppression noted at a ratio of one ThS-Ag to two Tm-BSA, and a slight suppression at the ratios of one ThS-Ag to five and ten TM-BSA. At one ThS-Ag to two TmS-Ag, a decrease in the stimulation index from nearly 15 to 5 was observed, while at this ratio no suppression of the response was noted in the culture with Tm-BSA. The differences in suppression effected by TmS-Ag versus Tm-BSA were statistically significant at all the tested ratios of 1:5 and 1:10 indicator to suppressor cells (p=0.04, 0.002). The results demonstrate that the autoantigen-induced suppression is specific at the T-cell level and that suppression is at least in part mediated by or dependent on T-cells of the suppressor phenotype.

Figure 4B:
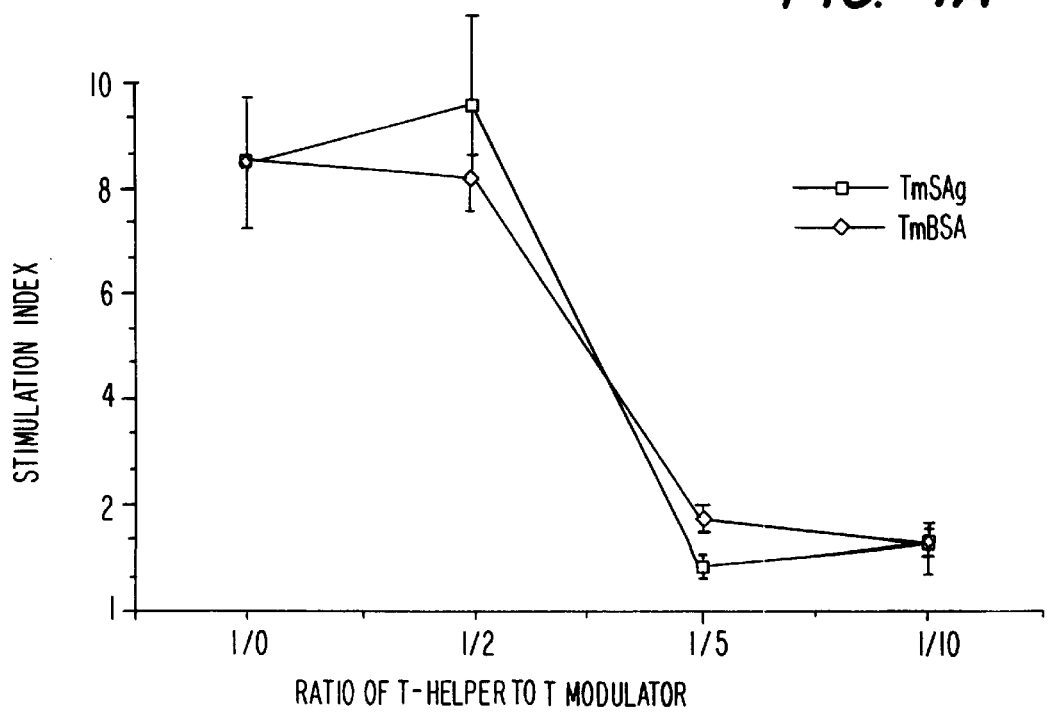
FIG. 4B demonstrates the response of ThSAg to ConA (a T-cell mitogen) with co-culture of TmSAg or TmBSA. Suppression was not noted at a ratio of one ThSAg to two splenocytes, while an identical degree of suppression was noted for both at higher ratios.

In contrast to the differences noted in FIG. 4A, FIG. 4B demonstrates the degree of suppression after TmS-Ag or Tm-BSA have been pre-incubated with Con A, (2 ug/ml). An essentially identical pattern of suppression can be noted for both TmS-Ag and Tm-BSA. These findings demonstrate the presence of an antigen-specific suppressor cell found in the spleen population of the S-Ag-fed Lewis rats.

Figure 4C:
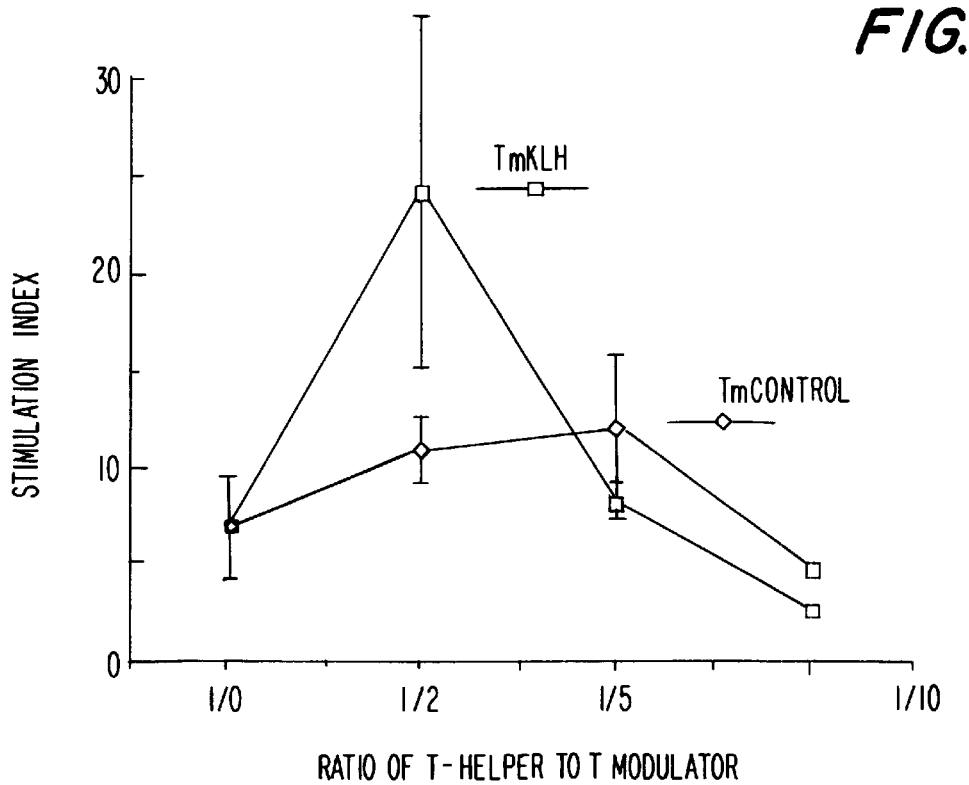
FIG. 4C shows the responses obtained by co-culturing ThS-Ag with splenocytes from animals fed KLH, i.e., keyhole limpet hemocyanin (such splenocytes being designated TmKLH) or nothing (designated Tm Control) and then pre-incubated in vitro with S-Ag.

FIG. 4C demonstrates the responses obtained with co-culturing ThS-Ag with TmKLH or Tm Control which have been preincubated for 48 hours with 5 ug/ml of S-Ag (but which were either not sensitized or sensitized with an unrelated antigen—KLH). As can be seen, no suppression of the ThS-Ag proliferative response was noted at ratios of one ThS-Ag to 5 or 10 TmKLH or Tm Control.

Figure 5:
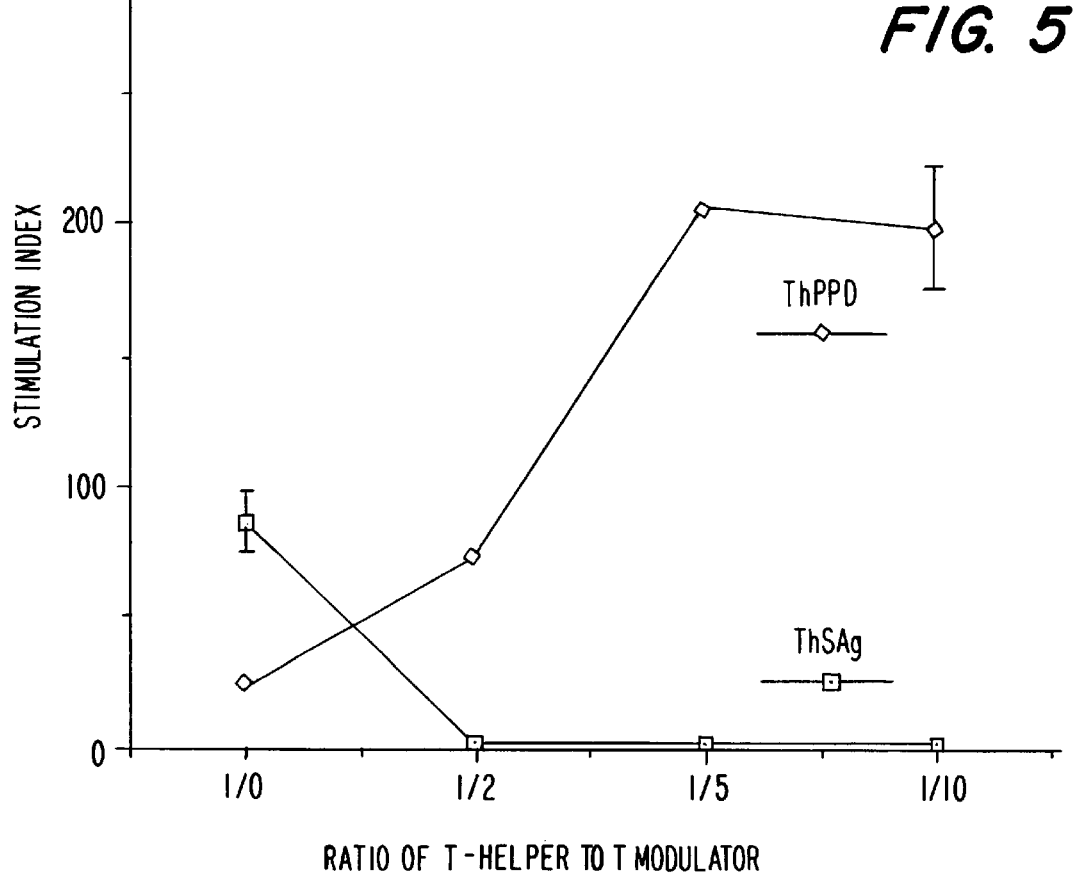
FIG. 5 shows the co-culturing of ThSAg or ThPPD (another indicator cell line specific for PPD) with TmSAg that had been pre-incubated in vitro with S-Ag. A profound suppression of the ThSAg response to S-Ag was seen, while an enhanced ThPPD proliferative response was noted to PPD.

FIG. 5 demonstrates the antigen-specific suppression obtained when TmS-Ag are pre-incubated with S-Ag (5 ug/ml) and then co-cultured with either ThS-Ag or ThPPD. A pronounced suppression of the proliferative response of ThS is seen at all ratios of splenocytes added. A strikingly different pattern was noted in the proliferative response of the PPD line. No suppression, but rather an augmentation of the proliferative response, was seen at all ratios of T-helper to splenocyte co-cultures tested. This phenomenon is related to the increased number of antigen presenting cells in the culture.

The capacity of the monoclonal antibody directed against the T-suppressor CD8+ subset (OX-8) to reverse the in vitro suppression (and thereby confirm T-suppressor involvement) was evaluated next. Table 1 demonstrates the results of such an experiment. The values in parenthesis are stimulation indices. A final concentration of 1:100 of each antibody was used and 25 ug/ml of S-Ag was added. A concentration of $1 \times 10^5$ TmS-Ag was used throughout this experiment.

TABLE 1

| ThS—Ag + APC | ANTIBODY | TmSAg* | S—Ag | CPM (SI) |
|---|---|---|---|---|
| + | – | – | – | 873 |
| + | – | – | + | 7011 (8.03) |
| + | OX-8 | – | – | 871 (1) |
| + | – | + | – | 1670 |
| + | – | + | + | 1888 (1.13) |
| + | OX-8 | + | + | 7247 (4.34) |
| + | LEU 2A | + | + | 1925 (1.15) |

*Added at 1:10 (ThSAg:TmSAg)

At a proportion of one ThS-Ag to 10 TmS-Ag cells, the proliferative response in the presence of S-Ag is reduced to a level approaching that of wells not containing antigen. However, in the presence of a 1:100 final dilution of the OX-8 antibody, the proliferative response is increased by four fold. The addition of the Leu 2a antibody at the same dilution did not reverse the suppression.

Using the cytofluorograph (Becton Dickinson, Franklin Lakes, N.J.), no difference in the total number of OX-8+ cells could be seen in the spleens of S-Ag-fed animals as opposed to the BSA-fed animals.

It has been shown in the present invention that oral feeding of the whole S-antigen molecule will lead to immune tolerance and the prevention of S-Ag-induced EAU. Further, antigen specific suppression of the immune response has been demonstrated in vitro. It has also been demonstrated that the anti-CD8 antibody directed to the CD8 suppressor/cytotoxic marker on the surface of lymphoid cells can block this suppression.

S-Ag-induced EAU is an experimental model for human uveitis that, in rats, can be induced by the transfer of CD4+ CD8– T lymphocyte lines to naive hosts (Caspi R. R., et al., supra; Gregorson, D. S., et al., *S-Antigen specific rat T cell lines mediate EAU and EAP,* in *Modern Trends in Immunology and Immunopathology of the Eye,* Secchi, A. G., and I. A. Fregona (eds), Masson, Milan, pp. 20–25, 1989). The dominant role of the T cell in this disorder and the predictive value of the EAU model for humans are further supported by the observation that cyclosporine can effectively prevent EAU in humans (Nussenblatt, R. B., et al., 1981, supra).

EXAMPLE 4

Effect of Feeding Retinal Autoantigen Against Clinical EAU

In this example, the effect of feeding the retinal autoantigen, S-Ag, against the clinical onset of EAU was investigated. Four groups of six female Lewis rats (n=24) weighing 180–200 grams were obtained from Charles River (Raleigh, N.C.). All immunizations were carried out beginning on day 0 as described above under MATERIALS AND METHODS: Antigens and Immunization. Feeding began on day 7 and continued on days 7, 9, 12 and 15. For Group P.O., 1 ug was administered orally, i.e., enterally (tube feeding) to the subjects. A saline solution was administered enterally to the Control Group. The degree of inflammation, if any, was read histologically by the masked observer method described above. The results for both the experimental (P.O.) and control groups are illustrated in FIGS. 6 and 7.

Figure 6:
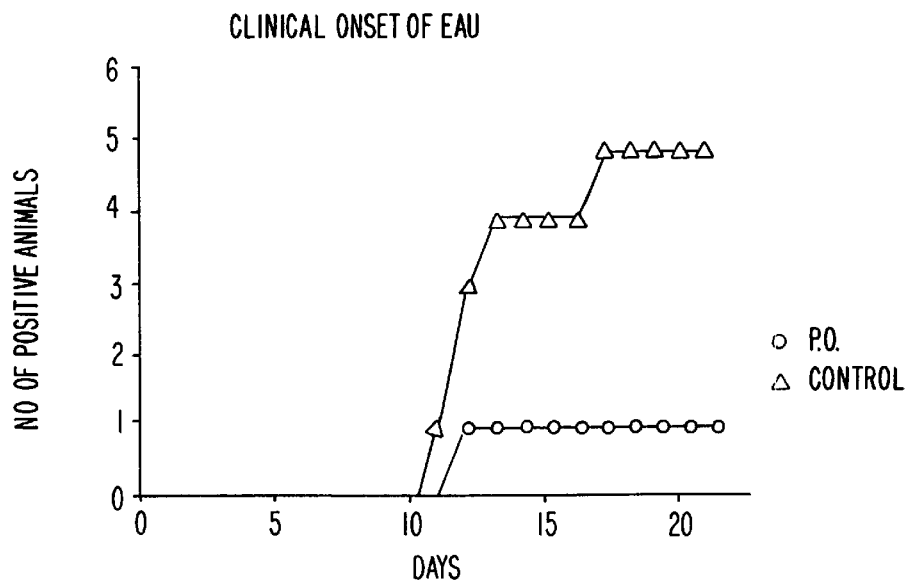
FIG. 6 depicts the pattern of disease onset (X-axis) in Lewis rat subjects over the course of a 21-day period. P.O. is the experimental group which were fed 1 mg S-Ag on days 7, 9, 12 and 15 following immunization with S-Ag on day zero.

It can be seen from FIG. 6 that 5 out of the 6 control group members developed disease 11–13 days after challenge. For the experimental P.O. group, only 1 out of 6 subjects developed disease and in this single instance, disease symptoms were mild compared to the disease in control rats.

Figure 7:
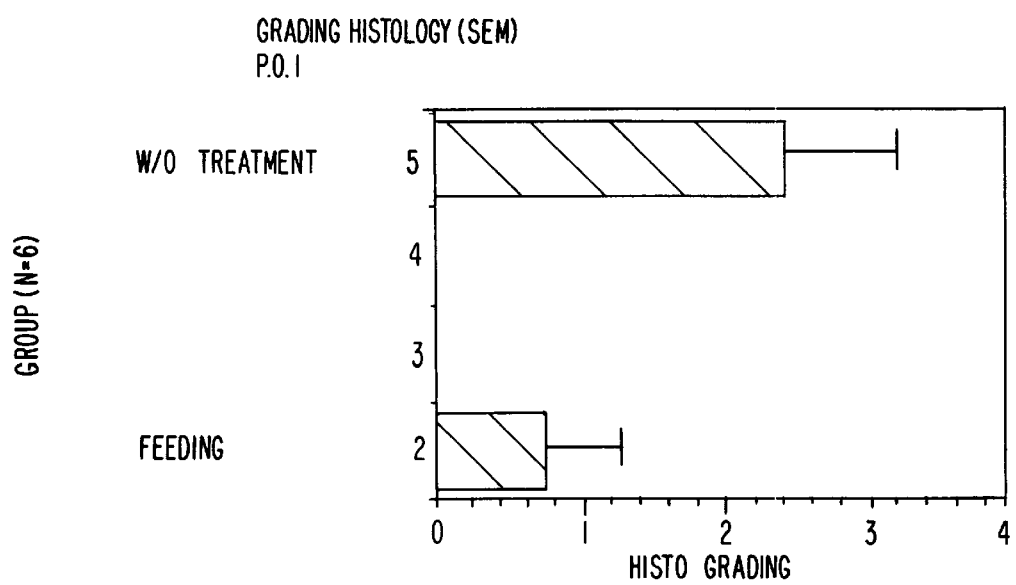
FIG. 7 depicts the degree of inflammation seen histologically in eyes of Lewis rats fed with S-Ag on days 7, 9, 12 and 15 following immunization with S-Ag on day zero. Results are of at least six animals and are presented as the means±standard-error-of-mean (SEM). Histologic Grading is the index of inflammation based upon criteria ranging from 0 (no evidence of inflammatory disease) to 4 (total destruction of retinal architecture).

FIG. 7 is a bar graph showing the results of histological grading, i.e., index of inflammation, of the groups. (See MATERIALS and METHODS: Antigens and Immunization Scheme for discussion of grading criteria) For the rat subjects receiving no treatment, the average grade was approximately 2.4 which corresponds midway between the 2+ (small exudative retinal detachment with larger destruction, mild to moderate number of cells in vitreous) and 3+ (retinal architecture beginning to be lost, larger exudative retinal detachment, moderate to large number of cells in vitreous). For the experimental P.O. subjects, the average grade was approximately 0.75 which is between 0.5 (trace evidence of inflammatory disease) and 1+ (focal areas of destruction with marked dropout of photoreceptors).

The present invention has been described above by reference to illustrative embodiments. Those skilled in the art will appreciate, however, that many additions, omissions and modifications to the subject matter described above are possible, all within the scope of the invention as claimed below.

EXAMPLE 5

Polypeptide Fragments Of The S-antigen Polypeptide For Use In The Present Invention Polypeptides having the amino acid sequences disclosed below may be orally or enterally administered to mammals for treating or preventing the clinical manifestations of a disease having the symptoms of uveoretinitis according to the present invention. The polypeptides are fragments of the S-antigen polypeptide. These polypeptides were chosen for use in treating or preventing uveoretinitis because they were found to induce uveoretinitis when administered to rats using the methods as described above on page 15. In addition, preliminary experiments have shown that T-cells isolated from rats suffering from uveoretinitis (which proliferated when exposed to the whole S-antigen polypeptide) did not proliferate when these fragments were administered to such cells in vitro using the system described above on page 18 (data not shown).

The amino acid sequences of these polypeptides are set forth below in Table 2 and their relative positions in the S-antigen polypeptide sequence are shown in FIGS. 8 and 9.

TABLE 2

Sequences of the Polypeptides:

Frag 3: SRDKSVTIYLGNRDYIDHVS
H-Ser-Arg-Asp-Lys-Ser-Val-Thr-Ile-Tyr-Leu-Gly-Asn-Arg-Asp-Tyr-Ile-Asp-His-Val-Ser-OH
Frag 6: VDPDLVKGKKVYVTLTCAFR
H-Val-Asp-Pro-Asp-Leu-Val-Lys-Gly-Lys-Lys-Val-Tyr-Val-Thr-Leu-Thr-Cys-Ala-Phe-Arg-OH
Frag 8: YGQEDVDVIGLTFRRDLYFS
H-Tyr-Gly-Gln-Glu-Asp-Val-Asp-Val-Ile-Gly-Leu-Thr-Phe-Arg-Arg-Asp-Leu-Tyr-Phe-Ser-OH
Frag 13: PFLLTFPDYLPCSVMLQPAP
H-Pro-Phe-Leu-Leu-Thr-Phe-Pro-Asp-Tyr-Leu-Pro-Cys-Ser-Val-Met-Leu-Gln-Pro-Ala-Pro-OH
Frag 18: KSSVRYLIRSVQHAPLEMGP
H-Lys-Ser-Ser-Val-Arg-Tyr-Leu-Ile-Arg-Ser-Val-Gln-His-Ala-Pro-Leu-Glu-Met-Gly-Pro-OH
Frag 32: ASSTIIKEGIDRTVLGILVS
H-Ala-Ser-Ser-Thr-Ile-Ile-Lys-Glu-Gly-Ile-Asp-Arg-Thr-Val-Leu-Gly-Ile-Leu-Val-Ser-OH
Frag 35: GFLGELTSSEVATEVPFRLM
H-Gly-Phe-Leu-Gly-Glu-Leu-Thr-Ser-Ser-Glu-Val-Ala-Thr-Glu-Val-Pro-Phe-Arg-Leu-Met-OH
Frag 36: VATEVPFRLMHPQPEDPAKE
H-Val-Ala-Thr-Glu-Val-Pro-Phe-Arg-Leu-Met-His-Pro-Gln-Pro-Glu-Asp-Pro-Ala-Lys-Glu-OH
Peptide GM: TSSEVATEVPFRLMHPQPED
H-Thr-Ser-Ser-Glu-Val-Ala-Thr-Glu-Val-Pro-Phe-Arg-Leu-Met-His-Pro-Gln-Pro-Glu-Asp-OH
Peptide G2:
SLTKTLTLVPLLANNRERRG=Bovine
SLTRTLTLLPLLANNRERAG=Human
H-Ser-Leu-Thr-Lys-Thr-Leu-Thr-Leu-Val-Pro-Leu-Leu-Ala-Asn-Asn-Arg-Glu-Arg-Arg-Gly-OH (Bovine)
H-Ser-Leu-Thr-Arg-Thr-Leu-Thr-Leu-Leu-Pro-Leu-Leu-Ala-Asn-Asn-Arg-Glu-Arg-Arg-Gly-OH (Human)
Peptide G3:
KEGIDKTVMGILVSYQIKVKL=Bovine
KEGIDRTVLGILVSYQIKVKL=Human
H-Lys-Glu-Gly-Ile-Asp-Lys-Thr-Val-Met-Gly-Ile-Leu-Val-Ser-Tyr-Gln-Ile-Lys-Val-Lys-Leu-OH (Bovine)
H-Lys-Glu-Gly-Ile-Asp-Arg-Thr-Val-Leu-Gly-Ile-Leu-Val-Ser-Tyr-Gln-Ile-Lys-Val-Lys-Leu-OH (Human)

FIG. 8 shows the human S-antigen polypeptide sequence in its entirety as disclosed in Shinohara, T. et al. (*Proc. Nat. Acad. Sci. USA* 84:6975–6979, 1987). FIG. 9 shows the sequences of bovine, human and mouse S-antigen polypeptides in their entirety as disclosed in Yamaki, K. et al (*FEBS Letters* 234: 39–43 and 236: 5071, 1988), Shinohara, T. et al. (supra) and Yamaki, K. et al. (*Biochem. Biophys. Res. Comm.* 142: 904–910, 1987), respectively, and the relative positions of polypeptides G2, G3 and GM of the present invention. The upper sequence in FIG. 9 is the bovine S-antigen polypeptide, the middle sequence is the human S-antigen polypeptide and the lower sequence is that of mouse S-antigen polypeptide. In addition, the relative positions of the M and N polypeptides disclosed above are also set forth in FIG. 9. It should be noted that polypeptide GM is from a region of the S-antigen polypeptide in which the bovine, mouse and human sequences are identical and polypeptides G2 and G3 are of bovine origin. The sequences of the human counterparts of these polypeptides are set forth above in Table 2. The human counterparts of polypeptides G2 and G3 are also expected to be useful in practicing the method of the present invention and are preferred when treating human patients suffering from a disease having the symptoms of uveoretinitis.

The peptides set forth in Table 2 above can be synthesized using well known solid phase synthesis techniques (Merrifield, R. B., *Fed. Proc. Am. Soc. Ex. Biol.* 21: 412, 1962 and *J. Am. Chem. Soc.* 85: 2149, 1963 and Mitchel, A. R., *J. Am. Chem. Soc.* 98: 7357, 1976.) Analogs of the polypeptides disclosed above can be synthesized as described on page 8 above. Alternatively, the polypeptides and their analogs can also be made by cloning the nucleic acid sequences encoding these polypeptides in suitable eukaryotic or prokaryotic hosts using genetic engineering techniques well known in the art.

The polypeptides disclosed above can be administered alone or in a combination containing any two or more of them to a mammal suffering from the symptoms of a disease having the characteristics of uveoretinitis. Administration of the peptides can be via the oral or enteral route according to the methods of the present invention. The effective amounts of the above-mentioned polypeptides for treating or preventing uveoretinitis are the same as those disclosed above on pages 12 and 13 of this specification.

EXAMPLE 6

Polypeptide Fragments of Inter-photoreceptor Retinoid Binding Protein for Use in the Present Invention Polypeptides having the amino acid sequences disclosed below also may be orally or enterally administered to mammals for treating or preventing a disease having the symptoms of uveoretinitis in accordance with the method of the present invention. The polypeptides disclosed below are fragments of the bovine Interphotoreceptor Retinoid Binding Protein (IRBP) disclosed above on p.8. The polypeptides, having the sequences HVDDTDLYLTIPTARSVGAADGS (alternatively referred to as R4) and PTARSVGAADGSSWEGVGVVPDV (alternatively referred to as R14) are amino acid sequence 1158–1180 and 1169–1191, respectively from the bovine IRBP as disclosed in Borst, D. E. et al (*J. Biol. Chem.* 264: 115, 1989).

These polypeptides can be produced as described below and above in Example 5 and can be administered orally or enterally according to the method of the present invention alone or in any combination of two or more with each other or with the polypeptides disclosed above in Example 5 in effective amounts (as disclosed above).

These polypeptides were chosen because, as shown below, lymphocytes isolated from a significant number of patients suffering from various eye disease of autoimmune etiology proliferated in response to these polypeptides. A description of the patients studied and the responses of lymphocytes isolated from these patients to the IRBP-derived polypeptides of the present invention is set forth below.

Patients participating in this study were seen in the uveitis clinic of the National Eye Institute, Bethesda, USA and at the Tokyo University Branch Hospital, Tokyo, Japan. All patients gave an informed consent prior to participating in the study. They were part of an ongoing protocol approved by each institution's committee on human investigation. All patients had active uveitis involving the posterior segment or had a history of prior active disease involving the retina or choroid. The patients tested had one of the following diagnosis: Behcet's disease, birdshot retinochoroidopathy, pars planitis, ocular sarcoid, sympathetic ophthalmia, and the Vogt-Koyanagi-Harada syndrome. The basis for the diagnosis of each is outlined elsewhere (Nussenblatt et al., *Uveitis: Fundamentals and Clinical Practice,* Year Book Medical Publishers, Chicago, Ill., 1989). Briefly, patients carrying the diagnosis of Behcet's disease met at least the minimal criteria for incomplete Behcet's set by the Behcet's Disease Research Committee of Japan (Behcet's Disease Committee of Japan, *Jpn. J. Ophthalmol. Research,* 18: 291, 1974) with all patients having ocular disease. Patients with birdshot retinochoroidopathy had cream colored lesions in the posterior segment as well as macular edema and retinal vascular changes. These patients were HLA A-29 positive as well. Patients with sympathetic ophthalmia had a history of penetrating trauma or multiple surgeries followed by a bilateral granulomatous uveitis. Vogt-Koyanagi-Harada syndrome patients had either Japanese or American Indian heritage, presenting with ocular and systemic changes compatible with the diagnosis. The ocular sarcoid patients had bilateral granulomatous uveitis accompanied in most cases by either a positive gallium scan or biopsy proven disease. Patients were tested irrespective of their current medical therapy (usually consisting of Cyclosporine and or Prednisone) or of their level of activity. Since the antigens tested were of retinal origin, anterior segment inflammation was not considered as part of the definition of active disease. The presence of retinal infiltrates, perivasculitis, snow banking or vitreous haze were accepted as evidence of activity. Additionally, cystoid macular edema when confirmed by fluorescein angiography was considered a sign of active disease. All the diagnostic categories were based on clinical criteria except in the case of ocular sarcoid and birdshot retinochoroidopathy where confirmation by another test was required. Control subjects were selected from either non-research staff or from clinic patients not being seen for a uveitis condition, and in whom a retinal or choroidal disorder had been ruled out.

Preparation of the Antigens

Antigens used in this assay included bovine interphotoreceptor retinoid binding protein purified to homogeneity as described by Redmond et al. (*Biochem.* 24: 787, 1985) and bovine S-antigen purified by the method described by Dorey et al. as described above. Interphotoreceptor retinoid binding protein derived peptides were synthesized and purified by a commercial laboratory (Applied Biosystems Inc., Foster City, Calif.) using the t-BOC chemistry, on a peptide synthesizer (430A, Applied Biosystems Inc.). The peptide sequences were derived from the sequence of bovine interphotoreceptor retinoid binding protein as determined and reported by Borst et al (supra). They consisted of sequence 1156–1180 (HVDDTDLYLTIPTARSVGAADGS) for R4 and of sequence 1169–1191 (PTARSVGAADGSSWEGVGVVPDV) for R14. S-antigen (M and N) polypeptides were synthesized in accordance with the method of Donoso and co-workers (supra), on a benzhydrylamine resin using an automated peptide synthesizer (SAM II; Biosearch, Inc., San Rafael, Calif.).

Lymphocyte Proliferation Assay

Proliferation assays were performed in the same way in Japan and the United States except where indicated. Briefly, mononuclear leukocytes from heparinized blood samples were separated on ISOLYMPH™ gradients (Gallard-Schlesinger, Carle Place, N.Y.) and cultured in RPMI-1640 medium with HEPES (GIBCO, Grand Island, N.Y.), supplemented with glutamine (2 mM), penicillin (100 units/ml), streptomycin (100 micrograms/ml) and heat inactivated human AB serum. 20% serum from a single donor was used in the cultures set up at the National Eye Institute while in assays carried out in Tokyo 10% commercial serum (Lot no.: 14510, Pel Freez, Brown Deer, Wis.) was used.

The cells were cultured using two methods. Briefly, in the first method, $2\times10^5$ cells/well were incubated in flat bottom 96-well plates for 5 days (as disclosed in Nussenblatt et al., *Am. J. Ophthamol.* 89: 173, 1980). Using the second method, which under certain circumstances was felt to increase responses by increasing cell to cell interactions, $5\times10^4$ cells/well were incubated in round bottom 96-well plates for 7 days (as disclosed in Hirose, S. et al., *Curr. Eye Res.* 7: 393, 1986). All cultures were in a total volume of 200 microliters and were set up in triplicate with or without stimulants. The antigen concentration was either 4, 20, 50 or 100 micrograms/ml. The cultures were incubated for the specified time at 37° C. with 100% humidity and 5% $CO_2$ in air, pulsed for the last 16 hrs with $^3$H-thymidine ($^3$H-TdR, New England Nuclear, Boston, Mass.; 2 Ci/mmol, 0.5 microCi/10 microliters/well) and harvested on glass fiber filters using a MASH II harvester. After drying, the filter pads were placed in vials with 3 ml toluene-based fluor and counted in a Beckman L3801 liquid scintillation counter. Several peptides were tested simultaneously; however, not all peptides could be tested on each patient. Cells from a normal control were usually tested simultaneously with cells from one or more patients.

Statistical Analysis

The mean of the triplicate cultures in counts per minute (CPM) was calculated for each set of replicate cultures. A stimulation index (S.I.) was derived by dividing the mean for each of the antigen stimulated cultures by the mean for the control cultures in which no antigen was added. For each testing center and for each antigen, a mean stimulation index±standard deviation was calculated for the control subjects. A significant response in a patient was considered to be present when the patient's stimulation index for a given peptide or determinant was above the mean for the controls by 2 standard deviations.

The stimulation indices for each tested antigen were also compared by disease category to the controls in order to determine if any statistically significant difference was present. Significance was assessed by using a standard non paired Student's 1 test. Patients were also assessed in regards to their clinical activity. Testing for statistical significance was done using Chi squared. Results are given as the mean stimulation index±standard error.

Patients

A total of 30 controls and 82 patients were tested, 47 patients were from the United States, and 35 patients from Japan. The characteristics of the U.S. and Japanese patients are set forth in Table 3 below.

The various disease entities responded differently to the uveitogenic antigens as shown in Table 4. However a similar

TABLE 3

| Clinical Entity | Testing Center | Mean Age (years) | Duration of Disease (months) | Number of Patients | Male/ Female | Clinical Activity Active/inactive | Therapy | | |
|---|---|---|---|---|---|---|---|---|---|
| | | | | | | | CSA | Pred | Cytotoxics |
| Behcet | U.S. | 34 (28–42)* | 50 (10–96) | 8 | 5/3 | 5/3 | 4 | 8 | |
| | Japan | 38 (24–60) | 64 (12–126) | 16 | 16/0 | 11/6 | 8** | 4 | 2 |
| Vogt-Koyanagi- | U.S. | 34 (24–60) | 33 (6–60) | 9 | 1/8 | 2/7 | 2 | 4 | |
| Harada | Japan | 47 (29–65) | 93 (4–247) | 10 | 5/5 | 0/10 | 1 | 7 | 1 |
| Sarcoid | U.S. | 60 (34–61) | 32 (7–72) | 9 | 8/1 | 5/4 | 2 | 4 | |
| | Japan | 45 (20–70) | 43 (2–180) | 9 | 3/8 | 6/3 | 0 | 5 | |
| Pars Planitis | U.S. | 31 (16–49) | 87 (30–48) | 6 | 2/4 | 5/1 | 2 | 3 | |
| Birdshot | U.S. | 56 (46–66) | 67 (24–106) | 9 | 6/4 | 1/8 | 2 | 2 | |
| Symp. Ophth. | U.S. | 52 (16–70) | 36 (6–72) | 6. | 2/4 | 4/2 | 1 | 6 | |
| Normal | U.S. | 36 (26–56) | | 20 | 10/10 | | | | |
| | Japan | 37 (14–87) | | 10 | 6/4 | | | | |

*Average. The range is given in parenthesis.
**Nine patients with Behcet's also received colchicine.

As can be seen in Table 3, the average age of the patients in both groups was comparable, being 41 years (range 10–70) for the American patients and 43 years (range 20–70) for the Japanese. The duration of follow-up also tended to be similar in the 2 groups: United States 44 months (92–108). Japan 57 months (2–247). On average, patients had been diagnosed with uveitis for 63 months (2–247). All patients seen in Japan were of Japanese descent; while in the American group, 41 of 47 were Caucasian, 5 were Black American and 1 patient was of Oriental extraction. The number of patients with clinically active disease varied among the various categories (Table 3) and between countries. Overall, half of the patients tested had active ocular disease. The largest discrepancy was found among sarcoid patients, where a greater number of the Japanese patients were active. Of all the groups, the birdshot retinochoroidopathy patients had the lowest incidence of activity, and none were tested in Japan where the disease is extremely rare. The proportion of active patients was highest among those suffering from Behcet's.

The responses of the patients' cells to the S-antigen polypeptide or IRBP polypeptides is set forth in Table 4 below.

response profile was found for the S-antigen polypeptide and interphotoreceptor retinoid binding protein. Patients with diseases involving the retina were more likely to give a significant proliferative response. In American patients, the mean proliferative responses to the S-antigen (20 micrograms/ml) were significant for Behcet's disease 2.8±1.0 (p=0.05) and birdshot retinochoroidopathy 2.7±0.2. For the interphotoreceptor retinoid binding protein (20 micrograms/ml), the proliferative responses tended to be lower, with a significant difference in Behcet's disease 1.5±0.4 (p=0.04), birdshot retinochoroidopathy 1.4±0.3 (p=0.04), and pars planitis 1.4±0.02 (p=0.04) as compared to controls (p.9±0.1). A similar pattern of response was present in the Japanese patients where the highest number of responders was found in Behcet's disease. The disease ocular sarcoid patients tested gave very few positive responders. However their responses to phytohemagglutinin and purified protein derivative were strong, indicating that the lack of response was not due to a generalized state of unresponsiveness, but probably reflected an inability to recognize bovine S-antigen or bovine interphotoreceptor retinoid binding protein. Culturing the cells for 7 days in round bottom wells increased the number of significant responses in some groups, but not in all. There was an

TABLE 4

| Antigen Tested | Behcet | | Vogt-Koyanagi- Harada | | Sarcoid | | Birdshot | Pars Planitis | Symp. Ophth. |
|---|---|---|---|---|---|---|---|---|---|
| | U.S. | Japan | U.S. | Japan | U.S. | Japan | U.S. | U.S. | U.S. |
| IRRP | 3/8* | 6/16 | 1/9 | 1/10 | 0/9 | 0/9 | 1/9 | 2/6 | 2/6 |
| | | | | 4/10{ | 3/9{ | | | | |
| R-4 | 4/8 | | 2/9}} | | 1/9 | | 5/9}} | 1/6}} | 2/6}} |
| R-14 | 2/8 | 2/16 | 2/9}} | 3/10 | 2/9†}} | 2/9 | 3/9}} | 1/6}} | 2/6 |
| S-Antigen | 3/8 | 3/16† | 4/9}} | 2/10† | 1/9† | 0/9 | 3/9 | 1/6 | 1/6 |
| M Peptide | 6/8 | 2/16† | 4/9 | 1/10† | 3/9 | 3/9† | 3/9 | 1/6 | 0/6 |
| N Peptide | 3/4}} | 6/16† | 1/4 | 5/10† | 0/4 | 7/9† | 4/9 | 0/6 | 1/6}} |

*The numerator refers to the number of positive responders. The denominator refers to the total number of patients tested. In most cases. 5 day cultures with 20 micrograms/ml of antigen in each well was found to be optimal except where indicated.
†Cells were cultured for 7 days.
}}Antigen concentration was 100 micrograms/ml.
{Cells were cultured with 4 micrograms/ml for 7 days.
**Nine patients with Behcet's also received colchicine.

increase in sensitivity mainly for patients with the Vogt

Koyanagi Harada syndrome. There was an increase in the number of significant responders to the S-antigen and the interphotoreceptor retinoid binding protein. The mean response to the S-antigen for lymphocytes from Vogt Koyanagi Harada patients in the United States was 2.8±1.4 as compared to controls (1.8±0.1), which was a statistically significant difference (p=0.03).

In addition to testing in vitro responses to the interphotoreceptor retinoid binding protein and the S-antigen polypeptide, the responses to polypeptide fragments of each of these antigens were determined. The results are set forth in Table 4 above.

As can be seen in Table 4, there was a correlation between the intensity of the proliferative response to the interphotoreceptor retinoid binding protein or the S-antigen polypeptide and the existence of a significant proliferative response to one or more of the polypeptide fragments of the present invention in five day cultures. If one considers only statistically significant responders to the S-antigen polypeptide, seven of nine American patients had a significant response to one or both peptide fragments tested (data not shown). In seven day cultures, 3 of 5 Japanese patients responsive to the S-antigen polypeptide had a response to either M or N peptide, or to both. In 6 of the 9 American patients that responded to the interphotoreceptor retinoid binding protein, there was a response to either R-4 or R-14, or to both. No such correlation was seen in the Japanese responders to interphotoreceptor retinoid binding protein.

Several patients' lymphocytes had a proliferative response to a polypeptide fragment, but did not recognize the parent antigen. In twelve of twenty-two American patients (54%) responding to one or the other S-antigen polypeptide fragment at 20 or 100 micrograms/ml in 5 day cultures, there was no cross reaction with the whole molecule. Under similar conditions, the responses to interphotoreceptor retinoid binding protein fragments gave no cross reaction in sixteen of twenty (84%) of American patients. The Japanese responders to S-antigen polypeptide fragments recognized the S-antigen polypeptide in only six of nineteen cases (cells cultured for 7 days).

Behcet's disease patients showed a response to fragments of both antigens but the responses were strongest for fragments or the S-antigen polypeptide M peptide at 20 micrograms/ml gave the highest response with a mean stimulation index of 5.3±1.0 for patients and 1.3±0.2 for controls (p=0.0001). The response to N peptide was also significant with patients having a mean stimulation index three times higher than controls. Birdshot retinochoroidopathy patients had similar responses to both sets of fragments. The mean stimulation indices in patients were twice those of controls for both sets of fragments.

Several patients demonstrated an ability to simultaneously give a significant proliferative response to at least one determinant of each antigen, but not necessarily to the whole antigen. A total of 32 patients out of the 82 patients tested (39%) were found to give such responses, 18 among the American patients and 14 among the Japanese. They were found in all disease categories but were more frequently found among the Behcet's disease and birdshot retinochoroidopathy patients. A similar distribution of cases was seen in the 2 countries. Eleven of the American patients were active at the time they gave a response to both antigens as compared to 6 of 18 non-responders (p=0.02). However there is little difference with the number of active patients (7/11 patients) responding to only one antigen (p=0.05). A correlation between active disease and a significant lymphoproliferative response was not seen among the Japanese patients.

In comparing the S-antigen polypeptide to interphotoreceptor retinoid binding protein, it appears that the S-antigen polypeptide is more frequently correlated with active disease (p=0.003). However, as is shown in Table 5 below, the profile in each disease entity was similar for the two antigens. An attempt was made to correlate proliferative responses with therapy, but no correlation was possible, patients with active disease were more likely to be treated with Cyclosporine or Prednisone.

TABLE 5

| Clinical Entity | Testing Center | IRBP | S-antigen |
| --- | --- | --- | --- |
| Behcet | U.S. | 2/7* | 3/7 |
|  | Japan | 6/9 | 3/4 |
| Vogt-Koyanagi-Harada | U.S. | 0/2 | 1/2 |
|  | Japan | 0/5 | 0/2 |
| Sarcoid | U.S. | 1/6 | 1/6 |
|  | Japan | 2/3 | 0/0 |
| Pars Planitis | U.S. | 2/5 | 2/5 |
| Birdshot | U.S. | 0/1 | 0/1 |
| Symp. Ophth. | U.S. | 1/4 | 2/4 |

*Numerator refers to those patients with active disease. The denominator refers to all patients with a significant proliferative response to the antigen at 20 micrograms/ml or 100 micrograms/ml. Data includes all responders with a stimulation index above 2.0 in both 5 and 7 day cultures.

What is claimed is:

1. A method of treating the disease uveoretinitis in a human in need of such treatment by suppressing an autoimmune response associated with said disease, the method comprising orally or enterally administering to said human an amount effective to suppress said response of at least one member selected from the group consisting of (i) an autoantigen; and (ii) a fragment of said autoantigen which when orally administered elicits regulatory T-cells in said human that recognize said autoantigen or said fragment.

2. The method according to claim 1, wherein said autoantigen comprises S-antigen.

3. The method of claim 2 wherein said member is a fragment of said S-antigen.

4. The method according to claim 2, wherein said S-antigen comprises a polypeptide of apparent molecular weight of about 48 kilodaltons.

5. The method according to claim 1, wherein said amount comprises from about 0.1 to about 15 mg/kg/day.

6. A method of treating the disease uveoretinitis in a human in need of such treatment by suppressing an autoimmune response associated with said disease, the method comprising orally or enterally administering to said human an effective amount for suppressing said response of at least one peptide selected from the group consisting of SRDKSVTIYLGNRDYIDHVS, VDPDLVKGKKVYVTLTCAFR, YGQEDVDVIGLTFRRDLYFS, PFLLTFPDYLPCSVMLQPAP, KSSVRYLIRSVQHAPLEMGP, ASSTIIKEGIDRTVLGILVS, GFLGELTSSEVATEVPFRLM, VATEVPFRLMHPQPEDPAKE, TSSEVATEVPFRLMHPQPED, SLTKTLTLVPLLANNRERRG, SLTRTLTLLPLLANNRERAG, KEGIDRTVLGILVSYQIKVKL KEGIDKTVMGILVSYQIKVKL, HVDDTDLYLTIPTARSVGAADGS and PTARSVGAADGSSWEGVGVVPDV.

7. The method of claim 6, wherein said effective amount ranges between about 0.1 mg/kg and about 15 mg/kg body weight of said human.

8. The method of claim 1 wherein said fragment of said autoantigen is selected from the group consisting of M-peptide and N-peptide of S-antigen.

9. A method of treating the disease uveoretinitis in a human in need of such treatment comprising orally or enterally administering to said human an amount of at least one member selected from the group consisting of (i) an autoantigen; and (ii) a fragment of said autoantigen which when orally administered elicits regulatory T-cells in said human, said amount being effective to accomplish at least one of (a) a decrease in stimulation index; (b) a decrease in inflammation of afflicted ocular tissue; (c) an improvement in visual acuity; (d) a reduction in cystoid macular edema; and (e) a decrease in the proliferative response of autoreactive T-cells of said human.

\* \* \* \* \*